US012755813B1

(12) United States Patent
Denton et al.

(10) Patent No.: US 12,755,813 B1
(45) Date of Patent: Oct. 6, 2026

(54) GENERATING VIRTUAL PERTURBED CELLS UTILIZING A LATENT TRANSFER PERTURBATION NEURAL NETWORK

(71) Applicant: Recursion Pharmaceuticals, Inc., Salt Lake City, UT (US)

(72) Inventors: Alisandra Kaye Denton, Montreal (CA); Berton Allen Earnshaw, Cedar Hills, UT (US); Cassandra Lynn Masschelein, Montreal (CA); Cian Eastwood, London (GB); Craig Terence Russell, Cambridge (GB); Hamed Shirzad, Vancouver (CA); Ihab Bendidi, Paris (FR); Jan Frederik Wenkel, Montreal (CA); Liam Duffy Hodgson, Montreal (CA); Lin Shuan Tu, Vancouver (CA); Shawn Tamajka Whitfield, Montreal (CA)

(73) Assignee: Recursion Pharmaceuticals, Inc., Salt Lake City, UT (US)

( * ) Notice: Subject to any disclaimer, the term of this patent is extended or adjusted under 35 U.S.C. 154(b) by 0 days.

(21) Appl. No.: 19/294,034

(22) Filed: Aug. 7, 2025

Related U.S. Application Data

(60) Provisional application No. 63/789,159, filed on Apr. 15, 2025.

(51) Int. Cl.
*G16B 40/00* (2019.01)
*G16B 50/10* (2019.01)

(52) U.S. Cl.
CPC ............. *G16B 40/00* (2019.02); *G16B 50/10* (2019.02)

(58) Field of Classification Search
None
See application file for complete search history.

(56) References Cited

PUBLICATIONS

Xu et al. (Cell Systems (2025—published online Apr. 4, 2025) vol. 16:23 pages).*
Lotfollahi et al. (Nature Methods (2019) vol. 16:715-721).*
Yang et al. (PLoS Computational Biology (2019) vol. 16(4):20 pages).*
Bunne et al. (Cell (2024) vol. 187:7045-7063).*
Yun et al. (Neural Information Processing Systems (NeurIPS) (2019); https://doi.org/10.48550/arXiv.1911.06455; 11 pages).*
DeDomenico (GigaScience (2017) vol. 6:1-8).*
Celik et al. (PLoS Computational Biology (2024) vol. 20(10):24 pages.*
Gonzalez-Ferrer et al. (Patterns (Apr. 11, 2025), vol. 6:3 pages.*
Lopez et al. (Nature Methods May 30, 2019:21 pages).*
Tang et al. (Journal of Advanced Research (2025) vol. 75:189-198; available online Oct. 31, 2024.*
Ajay Nadig, Joseph M Replogle, Angela N Pogson, Steven A McCarroll, Jonathan S Weissman, Elise B Robinson, and Luke J O'Connor. "Transcriptome-wide Characterization of Genetic Perturbations". In: bioRxiv, pp. 1-40, (2024).
Britt Adamson, Thomas M. Norman, Marco Jost, Min Y. Cho, James K. Nuñez, Yuwen Chen, Jacqueline E. Villalta, Luke A. Gilbert, Max A. Horlbeck, Marco Y. Hein, Ryan A. Pak, et al. "A Multiplexed Single-Cell CRISPR Screening Platform Enables Systematic Dissection of the Unfolded Protein Response". In: Cell 167.7, pp. 1867-1882, (2016).
Constantin Ahlmann-Eltze, Wolfgang Huber, and Simon Anders. "Deep Learning-Based Predictions of Gene Perturbation Effects Do Not Yet Outperform Simple Linear Methods". In: BioRxiv, pp. 2024-2009, (2024).
Daniel R. Wong, Abby S. Hill, and Robert Moccia. "Simple Controls Exceed Best Deep Learning Algorithms and Reveal Foundation Model Effectiveness for Predicting Genetic Perturbations". In: bioRxiv, pp. 1-24, (2025).
Diederik P. Kingma, Danilo J. Rezende, Shakir Mohamed, Max Welling. "Semi-Supervised Learning with Deep Generative Models". In: Advances in Neural Information Processing Dystems 27, pp. 1-9, (2014).
Eric Kernfeld, Yunxiao Yang, Joshua S. Weinstock, Alexis Battle, and Patrick Cahan. "A Systematic Comparison of Computational Methods for Expression Forecasting". In: BioRxiv, pp. 2023-07, (2023).
Gefei Wang, Tianyu Liu, Jia Zhao, Youshu Cheng, and Hongyu Zhao. "Modeling and Predicting Single-Cell Multi-Gene Perturbation Responses with scLAMBDA". In: bioRxiv, pp. 1-26, (2024).
Ihab Bendidi, Shawn Whitfield, Kian Kenyon-Dean, Hanene Ben Yedder, Yassir El Mesbahi, Emmanuel Noutahi, and Alisandra K. Denton. "Benchmarking Transcriptomics Foundation Models for Perturbation Analysis: one PCA still rules them all". In: arXiv preprint arXiv:2410.13956, 32 pages, (2024).
Mohammad Lotfollahi, Anna Kimovskaia Susmelj, Carlo De Donno, Leon Hetzel, Yuge Ji, Ignacio Ibarra, Sanjay R Srivatsan, Mohsen Naghipourfar, Riza M Daza, Beth Martin, et al. "Predicting Cellular Responses to Complex Perturbations in High-Throughput Screens". In: Molecular systems biology 19.6, e11517, pp. 1-19, (2023).
Petar Veličković, Guillem Cucurull, Arantxa Casanova, Adriana Romero, Pietro Liò, Yoshua Bengio. "Graph Attention Networks". In: International Conference on Learning Representations, pp. 1-12, (2018).

(Continued)

*Primary Examiner* — Lori A. Clow
(74) *Attorney, Agent, or Firm* — Keller Preece PLLC

(57) ABSTRACT

The present disclosure relates to systems, non-transitory computer-readable media, and methods for generating a digital perturbed cell with a plurality of virtual perturbed cell response features. More specifically, in one or more embodiments, the present disclosure relates to a flexible, modular latent transfer perturbation neural network that accurately generates virtual perturbed cells. To illustrate, in some embodiments, the disclosed systems utilize a base state neural network to generate a control cell latent representation based on a control cell. Further, the disclosed cells utilize a perturbation neural network to generate a perturbation latent representation based on a multi-perturbation data object. Additionally, in one or more embodiments, the disclosed systems combine the control cell latent representation and the perturbation latent representation and apply a neural network decoder to generate virtual perturbed cell response features.

20 Claims, 14 Drawing Sheets

(56) References Cited

PUBLICATIONS

Shaked Brody, Uri Alon, and Eran Yahav. "How Attentive are Graph Attention Networks?" In: International Conference on Learning Representations, pp. 1-26, (2021).
Yan Wu, Esther Wershof, Sebastian M Schmon, Marcel Nassar, Błażej Osiński, Ridvan Eksi, Kun Zhang, Thore Graepel. "PerturBench: Benchmarking Machine Learning 34 pages Models for Cellular Perturbation Analysis". In: arXiv preprint arXiv:2408.10609v2, (2024), 34 pages.
Yusuf Roohani, Kexin Huang, and Jure Leskovec. "Predicting Transcriptional Outcomes of Novel Multigene Perturbations with GEARS". In: Nature Biotechnology 42.6, pp. 927-935, (2024).

* cited by examiner

Ablation Study For Unseen Cell-Line

| | Standard 1108 | No Basal Matching 1110 | No Basal Averaging 1112 | No Basal Matching Or Averaging 1114 |
|---|---|---|---|---|
| No Basal Encoder 1102 | 0.469 | 0.413 | 0.468 | 0.413 |
| Multilayer Perceptron 1104 | 0.443 | 0.451 | 0.428 | 0.446 |
| Transcriptomic Embeddings + Multilayer Perception 1106 | 0.451 | 0.440 | 0.448 | 0.443 |

*Fig. 11*

GENERATING VIRTUAL PERTURBED CELLS UTILIZING A LATENT TRANSFER PERTURBATION NEURAL NETWORK

CROSS-REFERENCE TO RELATED APPLICATIONS

This application claims the benefit of, and priority to, U.S. Provisional Application No. 63/789,159, entitled "VeraPTOR: Predicting transcriptional outcomes for unseen perturbations using gene-gene relationships: A benchmark, method and analysis," filed Apr. 15, 2025, the contents of which are incorporated by reference herein in their entirety.

BACKGROUND

Recent years have seen developments in hardware and software platforms for training and utilizing machine learning models for generating predictions. For example, existing systems utilize large volumes of training data to teach machine learning models to generate intelligent predictions corresponding to complex biological interactions between genes, compounds, and/or cells. These approaches have the potential to transform the technical field of compound discovery through further technical innovations in machine learning. Despite these recent developments, existing systems suffer from a number of technical deficiencies, particularly with regard to accuracy, efficiency, and operational flexibility in implementing machine learning technologies.

BRIEF SUMMARY

Embodiments of the present disclosure provide benefits and/or solve one or more of the foregoing or other problems in the art with systems, non-transitory computer-readable media, and methods for generating a virtual perturbed cell utilizing a latent transfer perturbation neural network. More specifically, in one or more embodiments, the disclosed systems generate a control cell latent representation utilizing a base state neural network. Further, in some embodiments, the disclosed systems utilize a perturbation neural network to generate a perturbation latent representation from a multi-perturbation interaction data object. Additionally in one or more embodiments, the disclosed systems combine the control cell latent representation and the perturbation latent representation to generate a virtual perturbed cell latent representation. Further, in some embodiments, the disclosed systems utilize a neural network decoder to generate a virtual perturbed cell that reflects the perturbation from the perturbation latent representation.

Additional features and advantages of one or more embodiments of the present disclosure are outlined in the description which follows, and in part will be obvious from the description, or may be learned by the practice of such example embodiments.

BRIEF DESCRIPTION OF THE DRAWINGS

The detailed description provides one or more embodiments with additional specificity and detail through the use of the accompanying drawings, as briefly described below.

FIG. 11 illustrates results of an ablation study of modeling choices for an unseen cell line on an out-of-distribution task in accordance with one or more embodiments.

DETAILED DESCRIPTION

Figure 1:
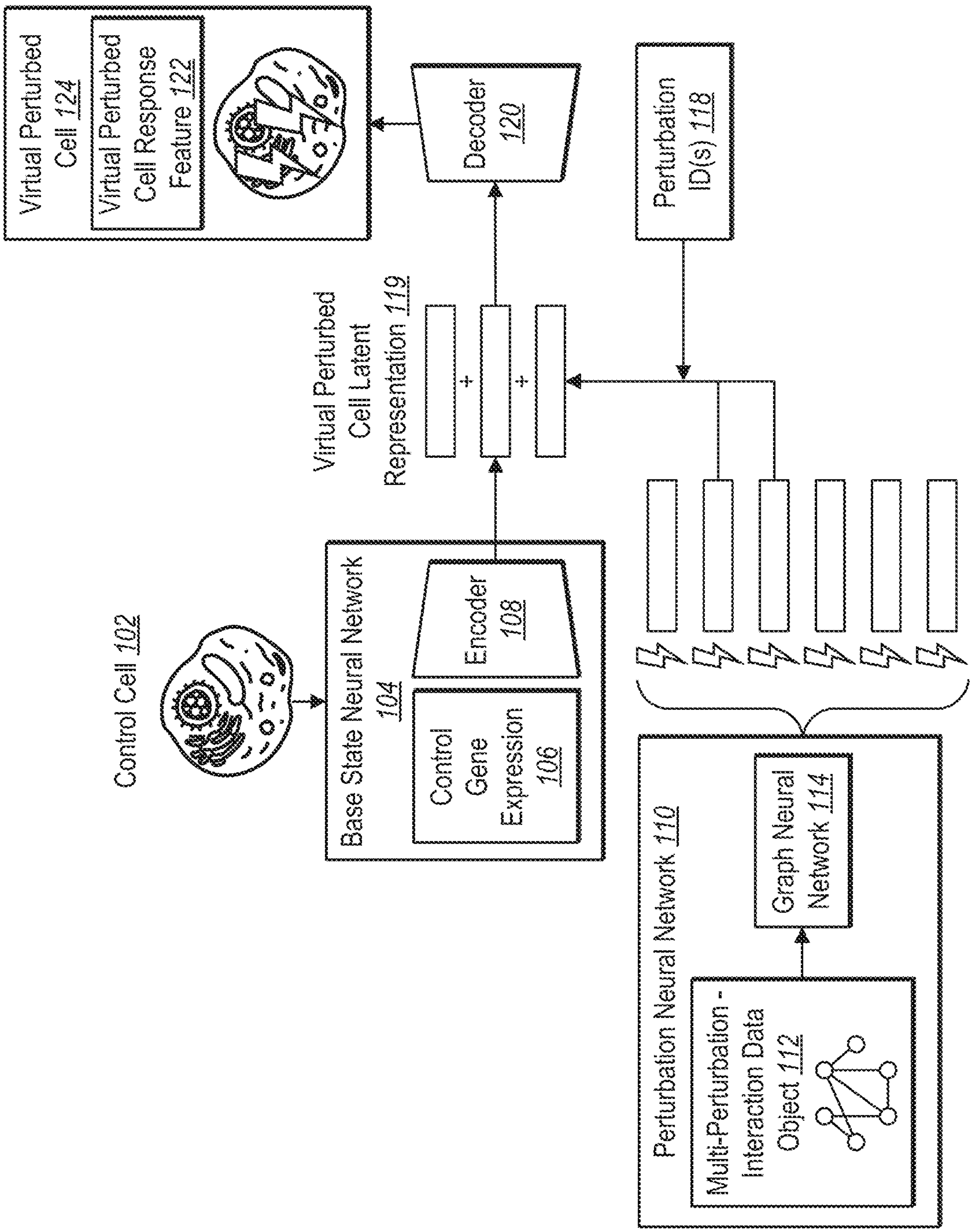
FIG. 1 illustrates a latent transfer perturbation neural network generating a virtual perturbed cell in accordance with one or more embodiments.

This disclosure describes one or more embodiments of a latent transfer perturbation system that accurately generates virtual perturbed cells reflecting a variety of different perturbations and cell types. More specifically, the latent transfer perturbation system utilizes a novel latent transfer perturbation neural network that integrates two complimentary pipelines: a base state neural network that determines a control cell latent representation, and a perturbation neural network that determines a perturbation latent representation by leveraging informative embeddings from gene interaction networks. Further, the latent transfer perturbation neural network combines these representations and decodes them to generate a virtual perturbed cell. Accordingly, the latent transfer perturbation system leverages biological data in a way that accurately generalizes for various cell lines and perturbation types-even those that were not utilized to train the latent transfer perturbation neural network.

As mentioned, the latent transfer perturbation system utilizes a base state neural network to generate a control cell latent representation. To illustrate, in one or more embodiments, the latent transfer perturbation system utilizes the base state neural network to extract features from a control cell. More specifically, the base state neural network captures intrinsic cellular attributes such as cell cycle stage, cell type, and other baseline phenotypic factors. In some implementations, the base state neural network maps a control cell's gene expression profile to the control cell latent representation as a compact, low dimensional embedding. Although the latent transfer perturbation system can utilize a variety of machine learning (neural network) architectures, in some embodiments, the base state neural network is an encoder such as a multilayer perceptron.

Further, in one or more embodiments, the latent transfer perturbation system utilizes a perturbation neural network to generate a perturbation latent representation. In one or more embodiments, the perturbation neural network includes trained graph neural networks that leverage biological knowledge graphs or other multi-perturbation interaction data objects to generate an embedding representations of one or more perturbations in a latent machine learning feature space. Accordingly, the perturbation neural network can generate perturbation latent representations that leverage perturbation interaction data from a variety of sources.

Additionally, in some embodiments, the latent transfer perturbation system combines the control cell latent representation and the perturbation latent representation to generate a virtual perturbed cell latent representation. To illustrate, in one or more embodiments, the latent transfer perturbation system utilizes both latent representations to perform latent shift where a decoder predicts features of a virtual perturbed cell from the given context. Accordingly, the latent transfer perturbation system generates a virtual perturbed cell latent representation the integrates control cell data from the control cell latent representation and perturbation data from perturbation cell latent representation.

In one or more embodiments, the latent transfer perturbation system also utilizes a neural network decoder within the latent transfer perturbation neural network to decode the virtual perturbed cell latent representation and generate a perturbed virtual cell. More specifically, in one or more embodiments, the latent transfer perturbation neural network utilizes a decoder to decode the virtual perturbed cell latent representation to determine a predicted gene expression profile (or other virtual perturbed cell response feature) for the indicated control cell. Accordingly, the latent transfer perturbation system can decode the virtual perturbed cell latent representation to generate a virtual perturbed cell reflecting an indicated control cell type and a predicted phenotypic response resulting from applying one or more indicated perturbations.

As mentioned previously, conventional systems have a number of technical problems with regard to accuracy and operational flexibility of neural networks, particularly in the unique technical context of generating virtual cells (and the related technical field of compound discovery pipelines). Indeed, many conventional perturbation prediction systems utilize either generative models to learn representations that can be perturbed or relationship networks with annotations. However, conventional perturbation prediction systems utilizing deep models for transcriptomic-focused perturbation biology have significant problems with accuracy. Many conventional perturbation prediction systems underperform even relative to simple or untrained baselines.

Further, many conventional perturbation prediction systems are trained on a per-dataset basis. To illustrate, many conventional systems require training for any and each cell line or other cell type individually. This creates major limitations in flexibility, as it limits conventional perturbation prediction systems' ability to generalize across biological contexts or scale in real-world applications. This is particularly limited in drug discovery settings, where performance across unseen perturbations, cell contexts, and experimental conditions is essential. Indeed, accurate machine learning predictions of phenotypic results from applying various perturbations revolutionizes conventional technical compound discovery processes. Conventional systems perform complex, robot-implemented assays to determine functional cellular responses from various perturbations, such as gene knockouts or compounds. Moreover, conventional systems perform additional analysis to determine concentration effects, toxicity, and other cellular response information to analyze the repercussions of applying compounds. Moreover, conventional systems utilize computationally expensive and time consuming processes for identifying potential gene targets that relate to particular diseases or compounds.

The latent transfer perturbation system improves accuracy relative to conventional systems by utilizing a latent transfer perturbation neural network that integrates two complementary modules: a base state neural network and a perturbation neural network (that includes graph learning approaches that can combine multiple perturbation data sources). Indeed, as outlined in additional detail below, the latent transfer perturbation neural network (including various combined graph representations with unique graph neural network analysis approaches) significantly outperforms the accuracy of conventional systems in predicting both in-distribution and out-of-distribution perturbations and cell lines, and in single and double perturbations. Indeed, as will be discussed in detail below with regard to FIG. 9 and FIGS. 10A-10B, the latent transfer perturbation neural network performs significantly better at predicting perturbations relative to available models.

The latent transfer perturbation system also improves flexibility relative to conventional systems by improving performance on out-of-distribution cell lines. For example, the latent transfer perturbation system improves the flexibility of the latent transfer perturbation neural network during training by tuning a matrix of node embeddings corresponding to perturbations as parameters. Additionally, by utilizing the perturbation neural network to learn biological knowledge encoded into multi-perturbation interaction data object such as gene interaction graphs, the latent transfer perturbation system is able to accurately apply perturbations to a variety of unseen cell lines. Accordingly, and as is discussed in detail below with regard to FIG. 9 and FIGS. 10A-10B, the latent transfer perturbation neural network is significantly more flexible with regard to unseen cell lines relative to conventional models.

In addition to significantly improving virtual perturbation cell production utilizing machine learning models, the latent transfer perturbation system also transforms the technical field of compound discovery pipelines. Indeed, by generating accurate virtual perturbed cells across various unseen cell lines, the latent transfer perturbation system can replace a variety of robot-implemented assays for measuring phenotypic responses of various perturbations. Moreover, the latent transfer perturbation system can streamline target identification processes by modeling cellular responses of various perturbations (e.g., compound or gene filtering perturbations) and identifying phenotypic similarities between genes and/or compounds.

In one or more embodiments, the latent transfer perturbation system generates virtual perturbed cells including one or more virtual perturbed cell response features utilizing a latent transfer perturbation neural network. FIG. 1 illustrates a latent transfer perturbation neural network generating a virtual perturbed cell based on a control cell and indicated perturbations. Indeed, FIG. 1 illustrates the latent transfer perturbation neural network including a base state neural network that generates a control cell latent representation, a perturbation neural network that generates a perturbation latent representation, and a neural network decoder that decodes a combination of the control cell latent representation and the perturbation latent representation to generate a virtual perturbed cell.

To illustrate, as shown in FIG. 1, the latent transfer perturbation system receives (or generates) an indication of a control cell 102 with corresponding control cell features (e.g., to analyze using a base state neural network 104). The control cell features can include a variety of descriptive or functional characteristics of a cell. In some implementations, the control cell features correspond to the features that will be modified/predicted for the virtual cell (e.g., virtual perturbed cell response features). To illustrate, in some implementations, the control cell features can include gene expression features (e.g., RNA/mRNA expression counts combined to form a gene expression profile) and the corresponding virtual perturbed cell response features can include predicted gene expression features in a virtual cell as a result of a perturbation. The control cell features (and predicted cell features) can include a variety of different features, including a cell state, epigenetic landscapes (e.g., chromatin accessibility, DNA methylation, or histone modification), protein expression or surface markers (e.g., proteomic signatures or surface antigen profiles), spatial localization, therapy efficacy, disease mutations, synthetic lethality, treatment resistance, metabolic activity, or functional programs (e.g., immune exhaustion, stemness).

In some embodiments, the latent transfer perturbation neural network receives the indication of the control cell 102 as data indicating control cell features. For example, in some embodiments, the latent transfer perturbation neural network receives the indication of the control cell 102 as high-dimensional input gene expression data. As shown in FIG. 1, the latent transfer perturbation system determines or retrieves a control gene expression 106 based on the indication of the control cell 102. The latent transfer perturbation system can analyze these cell features in a variety of forms. For example, in some implementations, the latent transfer perturbation system encodes the cell features utilizing one-hot encoding (or some other digital representation) and then feeds the cell features to the base state neural network 104.

As shown in FIG. 1, the latent transfer perturbation neural network utilizes the base state neural network 104 to generate a control cell latent representation from cell features of the control cell 102. As used herein, a control cell latent representation includes a digital numerical representation that reflects features of a control cell. In some embodiments, a control cell latent representation is a digital embedding (e.g., a in a latent machine learning feature space) reflecting one or more batch-matched control cell profiles.

To illustrate, in one or more embodiments, the base state neural network 104 includes a basal state encoder designed to capture intrinsic cellular attributes such as cell cycle state, cell type, and other baseline phenotypic features. In some embodiments, the base state neural network 104 maps a control cell's gene expression profile (or other features) $x \in \mathbb{R}^n$ to determine a control state latent representation as a compact, low-dimensional embedding as $s = f_{basal}(x) \in \mathbb{R}^d$.

The latent transfer perturbation system can utilize a variety of machine learning models. As used herein, a machine learning model includes or refers to a computer algorithm or a collection of computer algorithms that automatically improve for a particular task through experience based on use of data. For example, a machine learning model utilizes one or more learning techniques to improve in accuracy and/or effectiveness. Example machine learning models include various types of decision trees, support vector machines, Bayesian networks, decision trees, random forest models, or neural networks. Indeed, in some instances, a machine learning model includes a multilayer perceptron, transformer-based models (e.g., large language models), long short-term memory model, convolutional neural network (CNN) model, or recurrent neural network (RNN) model.

In addition, a neural network includes or refers to a machine learning model with artificial neurons trained and/or tuned based on inputs to determine or predict classifications, scores, or approximate unknown functions. For example, a neural network includes a model of interconnected artificial neurons (e.g., organized in layers) that communicate and learn to approximate complex functions and generate outputs based on a plurality of inputs provided to the neural network. In some cases, a neural network implements deep learning techniques to model high-level abstractions in data. A neural network includes various layers such as an input layer, one or more hidden layers, and an output layer that each perform tasks for processing data. For example, a neural network includes a diffusion neural network, a deep neural network, a convolutional neural network, a recurrent neural network (e.g., an LSTM), a graph neural network, a multilayer perceptron, or a large language model.

Thus, a perturbation neural network includes a neural network for analyzing a perturbation (e.g., a neural network for generating an embedding of a perturbation). Moreover, a base state neural network includes a neural network for analyzing a base state of a cell (e.g., a neural network for generating an embedding of a control cell). In one or more embodiments, the base state neural network 104 includes a multilayer perceptron to learn a direct deterministic mapping from high-dimensional input gene expression data to a fixed-size expression state.

In one or more embodiments, the latent transfer perturbation neural network utilizes the base state neural network 104 to align the control cell 102 with the predicted perturbed cell. More specifically, in one or more embodiments, the base state neural network 104 implements basal state matching where the control cell is selected to closely match the batch metadata of the corresponding perturbed sample. Further, as this matching is not unique, in one or more embodiments, the base state neural network 104 randomly samples one such appropriate control cell corresponding to the control cell 102. In addition, or in the alternative, in some embodiments, the base state neural network 104 utilizes basal state averaging to compute the average expression profile across all cells matching the cell line and/or batch corresponding to the control cell 102. As is discussed below with regard to FIG. 11, both basal state matching and basal state averaging can improve the accuracy of the latent transfer perturbation neural network.

Further, in one or more embodiments, the latent transfer perturbation system provides the control gene expression 106 to the base state neural network 104, which passes the control gene expression 106 through an encoder 108. Additionally, in some embodiments, the latent transfer perturbation neural network generates the control state latent representation from a control expression profile $x \in X \subset \mathbb{R}^n$, that has been aligned with the predicted cell with respect to cell line and batch effect.

In some embodiments, the encoder 108 utilizes transcriptomic foundation model embeddings to generate the control state latent representation. In addition, or in the alternative, the encoder 108 can include no basal state embeddings. In this configuration, the perturbation decoder learns a delta vector from the perturbation embedding, which is added to the control profile as $x \in \mathbb{R}^n$ such that $\hat{y}=x+g_\phi(s+\Sigma_{p \in P} z_p)$. The accuracy of these configurations is discussed in greater detail below with regard to FIG. 11.

As also shown in FIG. 1, the latent transfer perturbation neural network utilizes a perturbation neural network 110 to generate a perturbation latent representation. As used herein, a perturbation latent representation includes a digital numerical representation (in a latent machine learning feature space) that reflects features of one or more indicated perturbations. In some embodiments, a perturbation latent representation is a digital embedding (in a latent machine learning feature space) reflecting perturbation effects corresponding to one or more perturbations and relationships among those perturbations.

As used herein, the term perturbation (e.g., cell perturbation) refers to an alteration or disruption to a cell or the cell's environment (to elicit potential phenotypic changes to the cell). In particular, the term perturbation can include a gene perturbation (i.e., a gene-knockout perturbation) or a compound perturbation (e.g., a molecule perturbation or a soluble factor perturbation). These perturbations can be accomplished by performing a perturbation experiment/assay or modeled utilizing the latent transfer perturbation neural network to avoid the perturbation experiment. A perturbation experiment refers to a process for applying a perturbation to a cell. A perturbation experiment also includes a process for developing/growing the perturbed cell into a resulting phenotype.

As shown in relation to FIG. 1, the perturbation neural network 110 utilizes a multi-perturbation data object 112 and a graph neural network 114 to generate perturbation embeddings 116. As used herein, a multi-perturbation data object includes a digital data file or content item that comprises information or data regarding multiple perturbations (e.g., combined from multiple sources). For example, a multi-perturbation data object can include a database, array, matrix, or other data object that includes relationships between genes, between genes and compounds, and/or between compounds. In one or more embodiments, the multi-perturbation data object 112 is a biological gene-gene interaction knowledge graph. As shown, the latent transfer perturbation system can integrate an embedding of this graph with the basal state to produce the perturbed expression profile. Further, in one or more embodiments, the latent transfer perturbation system utilizes the perturbation latent representation as a set of perturbation tokens $P \subset \mathbf{P} := \{1, \ldots, N\}$.

In some embodiments, the latent transfer perturbation system generates the multi-perturbation data object by generating a perturbation interaction graph. Further, in one or more embodiments, the perturbation interaction graph includes nodes reflecting perturbations and perturbation interaction edges reflecting interactions between the perturbations. In some embodiments, the latent transfer perturbation system generates the perturbation interaction graph from various different sources of biological knowledge data, including databases and/or biological knowledge graphs.

In one or more embodiments, the perturbation neural network 110 includes a plurality of graph neural networks that leverage a plurality of knowledge graphs that capture gene-gene interactions to learn informative embeddings for gene perturbations. In some embodiments, the perturbation neural network 110 learns a matrix of node embeddings associated with perturbations tokens $\{1, \ldots, N\} \mapsto Z \in \mathbb{R}^{N \times d}$, with $N \in \mathbb{N}$ the number of perturbations relevant to the integrated task. Each row or node representation of this matrix represents the latent encoding of a specific perturbation. As will be discussed in greater detail below with regard to FIG. 7, the latent transfer perturbation system can utilize this input node feature matrix for training the latent transfer perturbation neural network.

Knowledge graphs can contain noisy or incorrect edges as false positives and/or have missing connections as false negatives. Further, knowledge graphs may have differing, and sometimes conflicting, data. To address these limitations, the latent transfer perturbation system can utilize an attention-based model like a graph attention network to dynamically re-weight neighbor importance within knowledge graphs. This improves the robustness of the perturbation neural network 110 by effectively down-weighting less credible connections.

A graph attention network includes a graph neural network that includes an attention mechanism. Instead of treating all neighbors equally within a graph, this attention mechanism can use a learned attention coefficient to weigh this contribution. Nodes within a graph attention network also attend to themselves. For example, each node can include its own features in the aggregation using multi-head attention.

Further, to address graph incompleteness and capture long-range dependencies, the latent transfer perturbation system utilizes graph transformers. A graph transformer includes a graph neural network that utilizes a transformer architecture in analyzing graph-structured data. A graph transformer can capture both local and global dependencies among nodes utilizing self-attention over nodes, positional encodings for graphs, edge feature integration, and global attention pooling. The latent transfer perturbation system can utilize a variety of graph transformer architectures (for example Exphormer) in the perturbation neural network 110. To illustrate, in one or more embodiments, the latent transfer perturbation system utilizes the graph transformers to direct attention within knowledge graphs beyond immediate graph neighbors. Thus, in some embodiments, the latent transfer perturbation system utilizes graph transformers to model implicit relationships and bridge structural gaps.

Further, in one or more embodiments, the perturbation neural network 110 includes a graph attention network hybrid model that allows for node-level attention weighting of information from different knowledge graphs. Indeed, in some embodiments, the latent transfer perturbation system generates two or more multi-perturbation interaction graphs from various sources, including from different data repositories. In some embodiments, the latent transfer perturbation system combines these multi-perturbation interaction graphs utilizing a graph attention network. More specifically, in some embodiments, the latent transfer perturbation system utilizes the graph attention network to dynamically weight the perturbation interaction edges from the multi-perturbation interaction graphs.

Additionally, as will be discussed in greater detail below with regard to FIGS. 2-6, in some embodiments, the perturbation neural network 110 includes a provenance-aware Exphormer MultiGraph variant and a multilayer extension of a graph attention network that leverages a supra-adjacency representation to effectively integrate information across multiple biological networks.

As also shown in FIG. 1, the latent transfer perturbation neural network utilizes perturbation ID(s) 118 to generate the perturbation latent representation. To illustrate, where $n \in \mathbb{N}$ denotes the number of experimentally measured genes and $N \in \mathbb{N}$ denotes the total number of observed perturbations in the data, the latent transfer perturbation neural network utilizes the perturbation ID(s) 118 to select node representations. More specifically, the latent transfer perturbation neural network utilizes the perturbation ID(s) 118 to select node representations from the perturbation embeddings 116 based on the multi-perturbation data object 112. In one or more embodiments, the latent transfer perturbation neural network utilizes these selected node representations as a perturbation latent representation.

Further, as shown in FIG. 1, the latent transfer perturbation system utilizes the latent transfer perturbation neural network to combine the control cell latent representation and the perturbation latent representation to generate a virtual perturbed cell latent representation 119. In one or more embodiments, the latent transfer perturbation neural network combines the information from the control cell latent representation and the perturbation latent representation to generate a virtual perturbed cell latent representation 119. In some embodiments, the latent transfer perturbation neural network predicts the transcriptional response $y \in Y \subset \mathbb{R}^n$ given a control cell latent representation and a perturbation latent representation. To illustrate, in one or more embodiments, the latent transfer perturbation neural network learns latent representations of both the control cell latent representation and the perturbation latent representation.

For example, as above, where the latent transfer perturbation neural network predicts the transcriptional response $y \in Y \subset \mathbb{R}^n$ where the latent transfer perturbation neural network generates the control state latent representation from a control expression profile $x \in X \subset \mathbb{R}^n$, and where a set of perturbation tokens is $P \subset P := \{1, \ldots, N\}$, the latent transfer perturbation neural network can combine the control cell latent representation and the perturbation latent representation as $x \mapsto s \in \mathbb{R}^d$ and $P \mapsto \{z_p \in \mathbb{R}^d : p \in P\}$ for a chosen latent dimension $d \in \mathbb{N}$.

Further, in one or more embodiments, the latent transfer perturbation neural network can combine the information via latent shift, where a learned decoder $g_\phi$ predicts the perturbation effect from the given context, i.e., $\hat{y} = g_\phi(s + \Sigma_{p \in P} z_p)$ using mean squared error (MSE) via Formula (1) below:

$$\mathcal{L}(y, \hat{y}) = \frac{1}{n} \|y - \hat{y}\|_2^2 \quad (1)$$

This process naturally integrates with single, double and more general multi-perturbation settings of order $m := |P|$ via the additive and compositional design. In some embodiments, the latent transfer perturbation system utilizes more sophisticated combination functions to learn transition functions $s' = T_\psi s, z)$ that allow sequential latent cell state modeling of subsequently applied perturbations, e.g., $\hat{y} = g_\phi(T_\psi(\ldots T_\psi(s, z_{p1}) \ldots, z_{p_1}))$. For example, in one or more embodiments, the latent transfer perturbation neural network leverages the base state neural network and the perturbation neural network to obtain s and $z_{p_1}$, $p \in P$.

As shown in FIG. 1, in one or more embodiments, the latent transfer perturbation neural network utilizes a decoder 120 to decode the virtual perturbed cell latent representation 119 and generate a virtual perturbed cell 124. As used herein, a decoder includes a machine learning model (e.g., neural network) trained to decode a latent machine learning representation to generate a predicted output. For instance, a decoder includes a neural network that generates a virtual perturbed cell from one or more virtual perturbed cell latent representations. As shown in FIG. 1, the virtual perturbed cell 124 includes a plurality of virtual perturbed cell response features 122.

As used herein, a virtual perturbed cell can refer to a digital representation including data indicating the effects of a perturbation on a cell. In some embodiments, a virtual perturbed cell includes a computational construct that reflect the effects of perturbations such as gene knockouts, biological or chemical treatments, signaling modifications, or other perturbations. In some embodiments, a virtual cell includes a plurality of response features indicating changes to the virtual perturbed cell as a result of the perturbation. In some embodiments, a virtual perturbed cell corresponds to a gene expression profile.

In one or more embodiments, as part of generation of the virtual perturbed cell 124, the latent transfer perturbation neural network generates a predicted gene expression profile for the virtual perturbed cell 124. More specifically, in one or more embodiments, the latent transfer perturbation neural network decodes the virtual perturbed cell latent representation to generate a predicted gene expression profile (or other cellular feature described herein). In some embodiments, a predicted gene expression profile includes gene activity and gene expression for a virtual perturbed cell. In one or more embodiments, a predicted gene expression profile includes predicted quantities, numbers, or counts of mRNA predicted to be active in a cell subject to the perturbation (e.g., active in a virtual perturbed cell).

As also used herein, a virtual perturbed cell response feature refers to a feature of a virtual perturbed cell in response to a perturbation. In some embodiments, the virtual perturbed cell response features 122 make up a log-transformed gene expression profile. For example, a perturbed cell response feature may include a molecular, functional, and/or phenotypic change relative to the corresponding control cell (e.g., a predicted response for a cell feature described herein). In addition, a perturbed cell response feature may include one or more features that are unchanged relative to the corresponding control cell.

Accordingly, the latent transfer perturbation system can utilize the latent transfer perturbation neural network to generate a virtual cell utilizing latent transfer to accurately predict perturbed cell response features for a virtual cell. Indeed, because the latent transfer perturbation neural network is able to combine and decode control cell data from the control cell latent representation and perturbation data from the perturbation latent representation, the latent transfer perturbation neural network is able to utilize weighted data from a variety of sources. This integration of data enhances the accuracy of the generated virtual perturbed cell 124.

Figure 2:
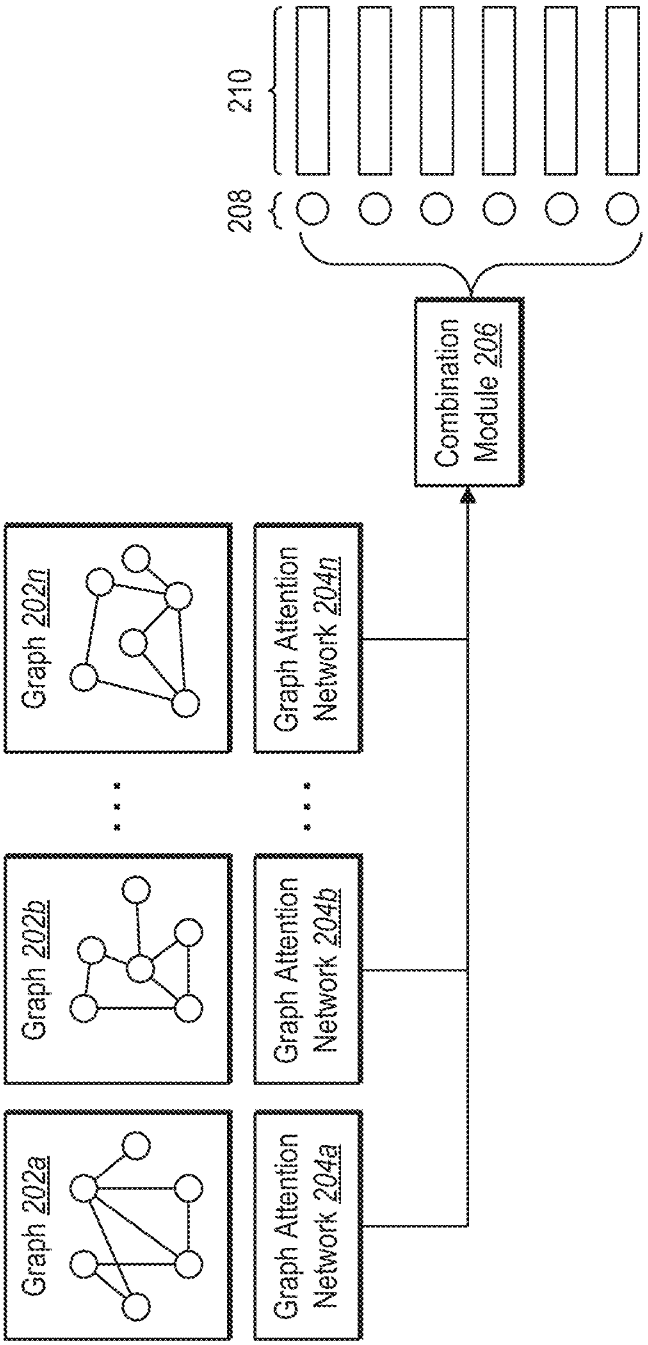
FIG. 2 illustrates generating and combining perturbation graphs in accordance with one or more embodiments.

For example, FIG. 2 illustrates an integration of graph data by the perturbation neural network in accordance with one or more embodiments. As shown in FIG. 2, in one or more embodiments, the latent transfer perturbation system utilizes a hybrid graph neural network architecture for the perturbation neural network in order to utilize perturbation data from various embedding graphs. More specifically, as shown in FIG. 2, the perturbation neural network utilizes hybrid graph neural network architecture that facilitates integration of perturbation embeddings that leverage a combination of biological knowledge graphs.

To illustrate, as shown in FIG. 2, the latent transfer perturbation system utilizes graphs 202_a_-202_n_. In some embodiments, the graphs 202_a_-202_n_ are multi-perturbation data objects. In some embodiments, a multi-perturbation data object is a biological interaction graph including nodes and edges reflecting perturbation data. For example, a multi-perturbation data object can include curated-database derived graphs and/or graphs derived from genome-wide perturbational screens.

In one or more embodiments, the latent transfer perturbation system extracts and utilizes perturbation machine learning embeddings from various sources, including from a functional response database. For example, in one or more embodiments, the latent transfer perturbation system extracts phenomic image machine learning embeddings and/or transcriptomic profile machine learning embeddings.

In some implementations, the latent transfer perturbation system generates phenomic image machine learning embeddings and/or transcriptomic profile machine learning embeddings. For example, the latent transfer perturbation system can capture or receive digital images of cells subject to one or more perturbations. The latent transfer perturbation system can utilize these phenomic digital images to generate embeddings. For instance, the latent transfer perturbation system can utilize a machine learning model (e.g., masked autoencoder) to generate phenomic image embeddings. Similarly, the latent transfer perturbation system can capture transcriptomic expression profiles from perturbed cells and generate transcriptomic embeddings from the transcriptomic expression profiles.

In some embodiments, the latent transfer perturbation system generate these embeddings using an embedding model described in UTILIZING MACHINE LEARNING MODELS TO SYNTHESIZE PERTURBATION DATA TO GENERATE PERTURBATION HEATMAP GRAPHICAL USER INTERFACES, U.S. patent application Ser. No. 18/526,707, filed Dec. 1, 2023 (hereinafter Application '707), which is incorporated by reference herein in its entirety, or UTILIZING MASKED AUTOENCODER GENERATIVE MODELS TO EXTRACT MICROSCOPY REPRESENTATION AUTOENCODER EMBEDDINGS, U.S. patent application Ser. No. 18/545,399, filed Dec. 19, 2023 (hereinafter Application '399), which is incorporated by reference herein in its entirety, or UTILIZING MASKED AUTOENCODER GENERATIVE MODELS TO EXTRACT CELLULAR RESPONSE REPRESENTATION EMBEDDINGS, U.S. patent application Ser. No. 19/074,095, filed Mar. 7, 2025, (hereinafter Application '095), which is incorporated by reference herein in its entirety, or GENERATING TRANSCRIPTOMIC BENCHMARKS FOR TRANSCRIPTOMIC MACHINE LEARNING MODELS UTILIZING A STRUCTURAL INTEGRITY METRIC, U.S. patent application Ser. No. 19/041,384, filed Jan. 30, 2025, (hereinafter Application '384), which is incorporated by reference herein in its entirety.

In some implementations, the latent transfer perturbation system stores these embeddings in a functional response database. The latent transfer perturbation system can extract perturbation machine learning embeddings (phenomic image machine learning embeddings or transcriptomic profile machine learning embeddings) from the functional response database;

- generating similarity metrics by comparing the perturbation machine learning embeddings; and
- generating the perturbation interaction edges utilizing the similarity metrics corresponding to the perturbation machine learning embeddings.

In one or more embodiments, a weighted graph G=(V, E, ω) has a set of n nodes (or genes) $V=\{v_1, \ldots, v_n\}$ and edges $E \subset V \times V$ representing gene-gene interactions and write υ~ω if {υ, ω}∈E, and N(υ)={ω∈E: υ~ω} Additionally, for the weighted graph, an edge weight $\omega: E \rightarrow \mathbb{R}$ characterizes the strength of the interaction. The derivation of the edge weight differs significantly between different graphs and data sources. In some embodiments, the perturbation neural network utilizes cosine similarity of embeddings for graphs derived from the maps ($\omega: E \rightarrow [-1,1]$), while literature-based graphs ($\omega: E \rightarrow [0,1]$) factor in information from experiments and the literature. The graph structure is maintained in the adjacency matrix $A \in \mathbb{R}$ according to Formula (2) below:

$$A = \left\{ \begin{matrix} \omega(e)\ iff & e = \{v, \omega\} \in E \\ 0 & \text{otherwise.} \end{matrix} \right\} \tag{2}$$

In one or more embodiments, the latent transfer perturbation system randomly initializes input node features (e.g., utilizing the Kaiming distribution). More specifically, in one or more embodiments, the latent transfer perturbation system draws the vectors $$h_v^0 \in \mathbb{R}^{d_0}$$

from this distribution and refines the vectors via backpropagation. In some embodiments, the Kaiming distribution reduces exploding and vanishing gradients. Further, in one or more embodiments, the latent transfer perturbation system concatenates the input node features across perturbations to form an input node feature matrix $H^0 \in \mathbb{R}^{N^{\star} \times d_0}$.

In some embodiments, the input node features for each perturbation are randomly initialized vectors $$h_v^0 \in \mathbb{R}^d$$

that are subsequently learned using backpropagation. The latent transfer perturbation system concatenates the input node features across perturbations to the input node feature matrix $H^0 \in \mathbb{R}^{n \times d}$. In addition, in one or more embodiments, the latent transfer perturbation system utilizes precomputed (and frozen) input node features.

The latent transfer perturbation neural network substantially improves perturbation prediction by incorporating multiple accurate biological graphs. Accordingly, as shown in FIG. 2, the latent transfer perturbation neural network utilizes the graph attention networks 204*a-n* to dynamically weight the edges of the graphs 202*a*-202*n*. Further, as shown in FIG. 2, the latent transfer perturbation system provides the weighted graphs 202*a*-202*n* to a combination module 206.

In one or more embodiments, the graphs 202*a*-202*n* include curated biological knowledge graphs and large-scale perturbation screens. To illustrate, in some embodiments, multi-perturbation data objects can constitute graphs or other data structures that include biological data such as perturbation data. For example, curated biological knowledge graphs can include a graph constructed by assigning edges between nodes that have a high Jaccard Index.

Additionally, by way of example, large-scale perturbation screens can include datasets linking genetic perturbation to either morphological or transcriptomic outcomes. Indeed, these large-scale perturbation screens can include data regarding cellular responses to stimuli that will enhance the accuracy of the latent transfer perturbation neural network. In some embodiments, to translate a perturbation screen into a graph, the latent transfer perturbation system utilizes derived embeddings to represent genes and cell lines in a high-dimensional space.

More specifically, in one or more embodiments, the latent transfer perturbation system generates a biological knowledge graph corresponding to a perturbation screen by computing a pairwise similarity score between all combinations of genes from the perturbation screen. More specifically, for each pair of genes ($g_i$, $g_j$), the latent transfer perturbation system determines cosine similarity between the aggregated embeddings $x_{gi}$ and $x_g$ utilizing Formula (3) below, where $x_{gi} \cdot x_{gj}$ represents the dot product of the vectors, $\|x_{gi}\|$ and $\|x_{gj}\|$ represent the Euclidian norms (magnitudes of vectors $x_{gi}$ and $x_{gj}$, respectively, and $x_{gik}$ and $x_{gjk}$ are the individual components of vectors $x_{gik}$ and $x_{gjk}$:

$$\text{cosine similarity } (x_{gi}, x_{gj}) = \frac{x_{gi} \cdot x_{gj}}{\|x_{gi}\| \|x_{gj}\|} = \frac{\sum_{k=1}^{n} x_{gik} x_{gjk}}{\sqrt{\sum_{k=1}^{n} x_{gik}^2} \cdot \sqrt{\sum_{k=1}^{n} x_{gjk}^2}} \tag{3}$$

In one or more embodiments, the latent transfer perturbation system converts these cosine similarities to their absolute values because the difference between highly cosine negative and highly cosine positive does not translate literally to the signed weight of the edge in a graph.

Further, in some embodiments, the latent transfer perturbation system utilizes a similarity threshold to determine which edges should be included in the graph. For example, the latent transfer perturbation system can utilize a threshold cosine similarity value for inclusion in the graph. In addition, or in the alternative, the latent transfer perturbation system can select a percentile range such as a top 1% or top 2% most similar edges. In another example, the latent transfer perturbation system can filter for a particular number of nodes by target, such as filtering for the most cosine similar edges that can be included while limiting the graph to twenty nodes. Additionally, in some embodiments, the latent transfer perturbation system arbitrarily assigns edge direction for undirected edges.

The combination module 206 combines the graphs 202*a*-202*n* to generate a perturbation latent representation 207, including perturbation nodes 208 and perturbation edges 210. As mentioned above, a perturbation latent representation includes data reflecting perturbations and perturbation interactions. More specifically, in some embodiments, the perturbation latent representation includes data reflecting perturbation effects and interactions among those perturbation effects.

The main graph neural network architecture of the perturbation neural network uses a graph attention network with $L \in \mathbb{N}$ layers, for Formula (4) and Formula (5) below:

$$H^\ell = f\left(H^{\ell-1}, A, W^\ell\right) \tag{4}$$

$$H^L = F\left(H^0\right) = f^L \circ f^{L-1} \circ \ldots \circ f^1\left(H^0\right) \tag{5}$$

In some embodiments, the latent transfer perturbation system utilizes graph attention networks 204*a*-204*n* having four-layers. Accordingly, in such embodiments, the perturbation latent representation 207 includes attention information for each node four steps away within the perturbation latent representation 207. Further, in one or more embodiments, the latent transfer perturbation system utilizes a four-layer architecture with hidden dimension d=64 for the perturbation neural network.

In some embodiments, the perturbation neural network utilizes a graph attention transformer model to aggregate information during message passing across the intra-layer connections and the inter-layer connections of the unified supra-adjacency representation to generate the perturbation latent representation from the unified supra-adjacency representation. For every edge, the perturbation neural network learns an attention score that characterizes its importance that is then normalized at every node across incoming edges. On the node level, the latent transfer perturbation system updates the features of $\in V$ according to Formula (6) below:

$$h_v^\ell = \sigma\left(\sum_{u \in N(v)} \bar{a}_{uv} W^\ell h_u^{\ell-1}\right) \tag{6}$$

Further, in one or more embodiments, to derive the attention scores $\bar{a}_{uv} = \text{ATT}_\theta(h_u, h_v)$, the latent transfer perturbation system utilizes Formula (7) and Formula (8), below:

$$a_{uv} = \theta^\top \sigma([Wh_u \| Wh_v]), \tag{7}$$

$$\bar{a}_{uv} = \text{softmax}(a_{uv} \mid N(v)) = \frac{\exp(a_{uv})}{\sum_{\omega \in N(v)} \exp(a_{\omega v})}. \tag{8}$$

Figure 3:
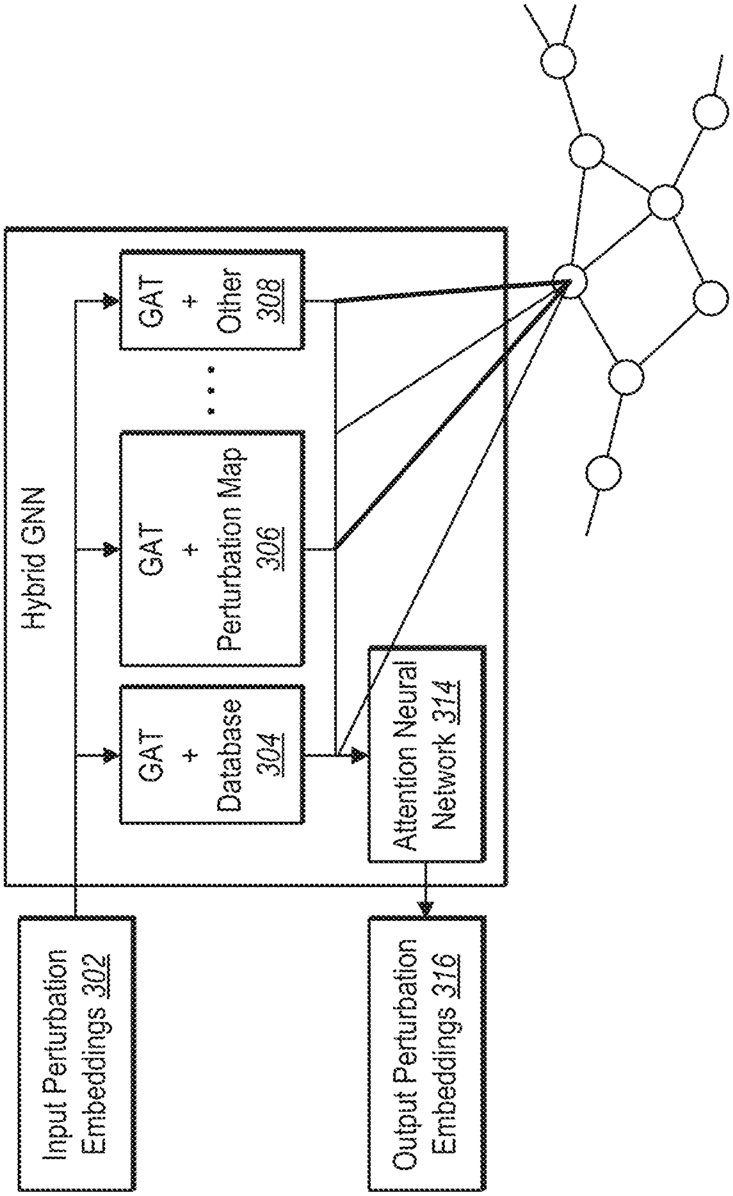
FIG. 3 illustrates utilizing a hybrid graph neural network to generate perturbation embeddings in accordance with one or more embodiments.

In some embodiments, the perturbation neural network is a hybrid graph neural network. FIG. 3 illustrates additional detail regarding the hybrid graph neural network architecture of the perturbation neural network in accordance with one or more embodiments. To illustrate, the hybrid graph neural network 300 architecture facilitates the perturbation neural network in learning perturbation embeddings from various multi-perturbation data objects. Indeed, as mentioned above, in some embodiments, the perturbation neural network utilizes a data-driven node level attention mechanism.

As shown in FIG. 3, the hybrid graph neural network 300 receives input perturbation embeddings 302. Further, as shown in FIG. 3, the hybrid graph neural network 300 utilizes graph attention networks to modify and/or generate graphs from various data sources. For example as shown in FIG. 3, the latent transfer perturbation system applies a graph attention network to a database 304, a perturbation map 306, and other data 308. In one or more embodiments, for a set of graph neural network channels $\mathcal{F} = \{F_1, \ldots, F_K\}$, the latent transfer perturbation system aggregates the outputs of each channel $\{H^F : F \in \mathcal{F}\}$.

Additionally, as shown in FIG. 3, the hybrid graph neural network 300 provides the attention-weighted perturbation embeddings through an attention neural network 314. In some embodiments, the latent transfer perturbation system calculates node-to-channel attention scores as $s_F: V \rightarrow \mathbb{R}$, utilizing Formula (9) below:

$$s_F(v) = v^1 \sigma\left(\left[Wh_v^F \| Wh_v^F\right]\right) \tag{9}$$

Additionally, in some embodiments, the latent transfer perturbation system normalizes the attention scores using the Softmax function across channels rather than across nodes utilizing $\bar{s}_F(v)=\mathrm{softmax}(s_F(v)|\mathcal{F})$. Further, in some embodiments, the latent transfer perturbation system determines the aggregated perturbation embeddings by weighting channels according to their attention score using Formula (10) below:

$$h_v = \sum_{F\in\mathcal{F}} \bar{s}_F(v) W h_v^F \tag{10}$$

Additionally, in some embodiments, the latent transfer perturbation system applies a multi-layer perceptron to the perturbation embeddings, $$h'_v = MLP(h_v).$$

Both attention mechanisms in the graph attention network 314 and the hybrid graph neural network 300 are compatible with multi-head attention. Accordingly, in one or more embodiments, the latent transfer perturbation system can utilize the hybrid graph neural network 300 to determine output perturbation embeddings 316. Thus, in some embodiments, the latent transfer perturbation system utilizes the hybrid graph neural network 300 to determine perturbation nodes and perturbation edges for biological knowledge graphs that introduce inductive bias to the perturbation neural network.

Figure 4:
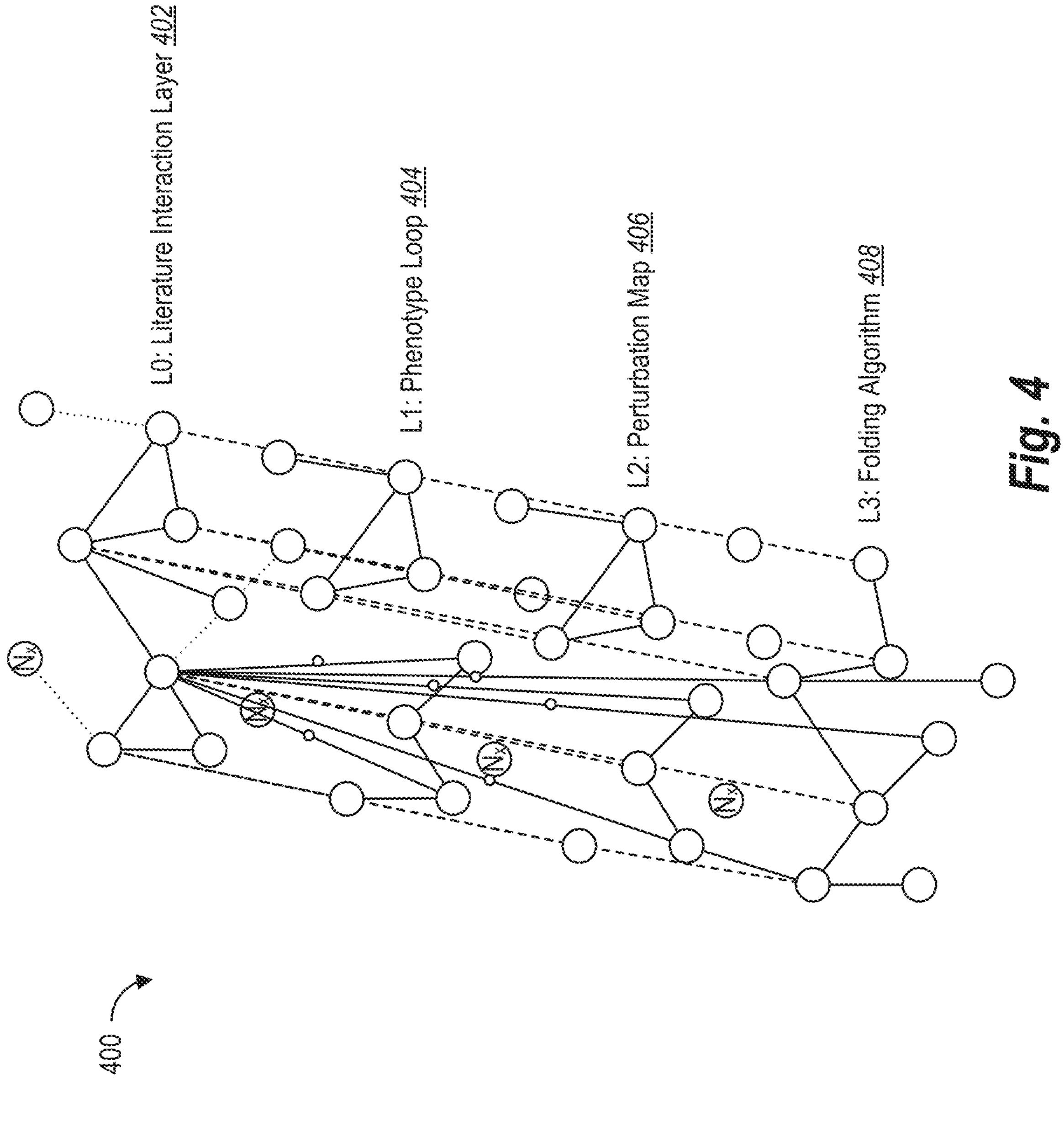
FIG. 4 illustrates layers of a graph neural network in accordance with one or more embodiments.

Additionally, in one or more embodiments, the perturbation neural network of the latent transfer perturbation neural network is a multilayer graph neural network. FIGS. 3-4 illustrate additional detail for the structure and pipeline of a multilayer graph neural network. More specifically, FIG. 3 illustrates the structure of the multilayer graph neural network.

As shown in FIG. 3, the multilayer graph neural network 400 includes various layers of nodes with connecting edges. More specifically, as shown in FIG. 4, the multilayer graph neural network 400 includes a literature interaction layer 402 with perturbation nodes reflecting perturbation data from one or more databases, written descriptions, or other formats. Further, in some embodiments, the multilayer graph neural network 400 includes a phenotype layer 404 that reflects node embeddings from one or more phenomic graphs. Additionally, in some embodiments, the multilayer graph neural network 400 includes a perturbation map layer 406 that reflects node embeddings from a transcriptomics map or knowledge graph. Further, in some embodiments, the multilayer graph neural network includes a folding algorithm layer 408 that reflects node embeddings based on a protein structure algorithm such as Alphafold.

As shown in FIG. 3, the multilayer graph neural network 400 includes various node edges between the nodes of the layers 402-408. Indeed, the multilayer graph neural network 400 includes node edges both within layers and between layers. Accordingly, many nodes have neighbors in other layers of the multilayer graph neural network 400.

In one or more embodiments, given a set $\mathcal{V}$ of entities and a set $\mathcal{L}=\{\mathcal{L}_1, \ldots, \mathcal{L}_\ell\}$ of layers, a multilayer network is denoted with $\mathcal{G}_\mathcal{L}=\langle V_\mathcal{L}, E_\mathcal{L}, \mathcal{X}, \mathcal{V}, \mathcal{L}\rangle$, where $V_\mathcal{L} \subseteq \mathcal{V}\times L$ is the set of all entity occurrences, or nodes, in $\mathcal{L}$. Further, $V_l$ is the set of nodes in layer $l(l\in\mathcal{L})$. $E_\mathcal{L}$ is the set of edges between nodes belonging to the same layer, and $E_1 \subseteq V_l \times V_l$ is the set of edges in layer l. Additionally, each entity has a node in at least one layer, hence $\mathcal{V}=\bigcup_{l=1..\ell} V_l$ and inter-layer edges exist between each node in a layer and its counterpart in a different layer.

Accordingly, in one or more embodiments, the latent transfer perturbation system represents the multilayer graph neural network 400 by a set of adjacency matrices $\mathcal{A}=\{A_1, \ldots, A_\ell\}$, with $A_l \in \mathbb{R}^{n_l\times n_l}(l\in L)$, where $n_l=|V_l|$. Further, the latent transfer perturbation system can associate entities with external information or attributes stored in layer-specific matrices $\mathcal{X}=\{X_1, \ldots, X_\ell\}$, where $X_l$ is the attribute matrix for layer l. If no attributes are given for nodes in a layer, the latent transfer perturbation system can randomly initialize the nodes.

In one or more embodiments, the multilayer graph neural network 400 includes a supra-adjacency representation, which encodes both intra-layer and inter-layer connections in a unified graph structure. Accordingly, the latent transfer perturbation system can leverage a graph attention network mechanism while capturing the multilayer representation of the data.

In some embodiments, the multilayer graph neural network 400 learns the node features for each gene representation through an embedding layer. Specifically, in one or more embodiments, the multilayer graph neural network 400 represents each node in each layer with a learnable embedding vector. Further, in some embodiments, the multilayer graph neural network 400 constructs a unified supra-adjacency representation that encodes intra-layer and inter-layer connections of a plurality of multi-perturbation interaction graphs. Formally, given $\ell$ distinct layers, where $A_i$ is the adjacency matrix for layer i, and $I_{i,j}$ is a matrix defining the inter-layer connections between layers i and j, typically identity matrices that connect the same entity across different layers, the latent transfer perturbation system can define the unified supra-adjacency representation $A_S$ as:

$$A_S = \begin{pmatrix} A_1 & I_{1,2} & \ldots & I_{1,\ell} \\ I_{2,1} & A_2 & \ldots & I_{2,\ell} \\ \vdots & \vdots & \ddots & \vdots \\ I_{\ell,1} & I_{\ell,2} & \ldots & A_\ell \end{pmatrix}$$

In one or more embodiments, using this representation, the latent transfer perturbation system applies a graph attention transformer model to learn node embeddings. More specifically, for a node v in the supra-adjacency graph, the latent transfer perturbation system can find its feature update at layer k of the multilayer graph neural network 400 utilizing Formula (11) below:

$$h_v^{(k)} = AGG_{q=1}^{Q}\left(\sum_{u\in N(v)} \alpha_{(v,u)}^{(q,k)} W^{(q,k)} h_u^{(k-1)}\right) \tag{11}$$

For Formula (11), $\mathcal{N}(v)$ represents all neighbors of node v in the supra-adjacency graph (including both intra-layer and inter-layer connections), $$a_{(v,u)}^{(q,k)}$$

is the attention coefficient between nodes v and $u$ for the q-th attention head at the k-th layer, $W^{(q,k)}$ is the learned weight matrix, and $$h_u^{(k-1)}$$

is the feature vector of node $u$ from the previous layer.

Additionally, in one or more embodiments, the latent transfer perturbation system determines attention coefficients utilizing Formula (12), below:

$$a_{(v,u)}^{(q,k)} = \frac{\exp\left(LeakyReLU\left(a^{q,k)T}\left[W^{(q,k)T} h_v^{(k-1)} \middle\| W^{(q,k)} h_u^{(k-1)}\right]\right)\right)}{\sum_{\omega \in N} \exp\left(LeakyReLU\left(a^{(q,k)T}\left[W^{(q,k)T} h_v^{(k-1)} \middle\| W^{(q,k)} h_\omega^{(k-1)}\right]\right)\right)} \quad (12)$$

Further, where $a^{(q,k)}$ is the attention vector the q-th head at the k-th layer, and || represents concatenation, for the aggregation function across attention heads, the latent transfer perturbation system can utilize Formula (13), below:

$$AGG_{q=1}^{Q}\begin{cases} CONCAT_{q=1}^{Q}\left(h_v^{(q,k)}\right), & \text{if aggregation} = \text{'}concat\text{'} \\ \frac{1}{Q}\sum_{q=1}^{Q} h_v^{(q,k)}, & \text{if aggregation} = \text{'}avg\text{'} \end{cases} \quad (13)$$

In one or more embodiments, after propagating information through multiple graph attention network layers, the latent transfer perturbation system extracts the final layer embeddings, which capture both local and global structural information across a perturbation neural network. Accordingly, these embeddings serve as comprehensive representations of each gene's perturbation effect in the context of multiple biological interaction networks.

Thus, the multilayer graph neural network 400 provides a perturbation modeling approach that is robust to heterogeneous network structures and can effectively capture cross-layer dependencies between genes. By simultaneously considering multiple biological interaction networks, the latent transfer perturbation system learns comprehensive gene embeddings that reflect both pathway-specific and global effects of perturbations. This enables more accurate predictions for unseen single perturbations, where the model can leverage information from related genes across different layers. Moreover, for double perturbations, the latent transfer perturbation neural network effectively captures the complex non-linear effects that emerge from simultaneous modifications of multiple genes, even when these specific combinations were not observed during training.

Figure 5:
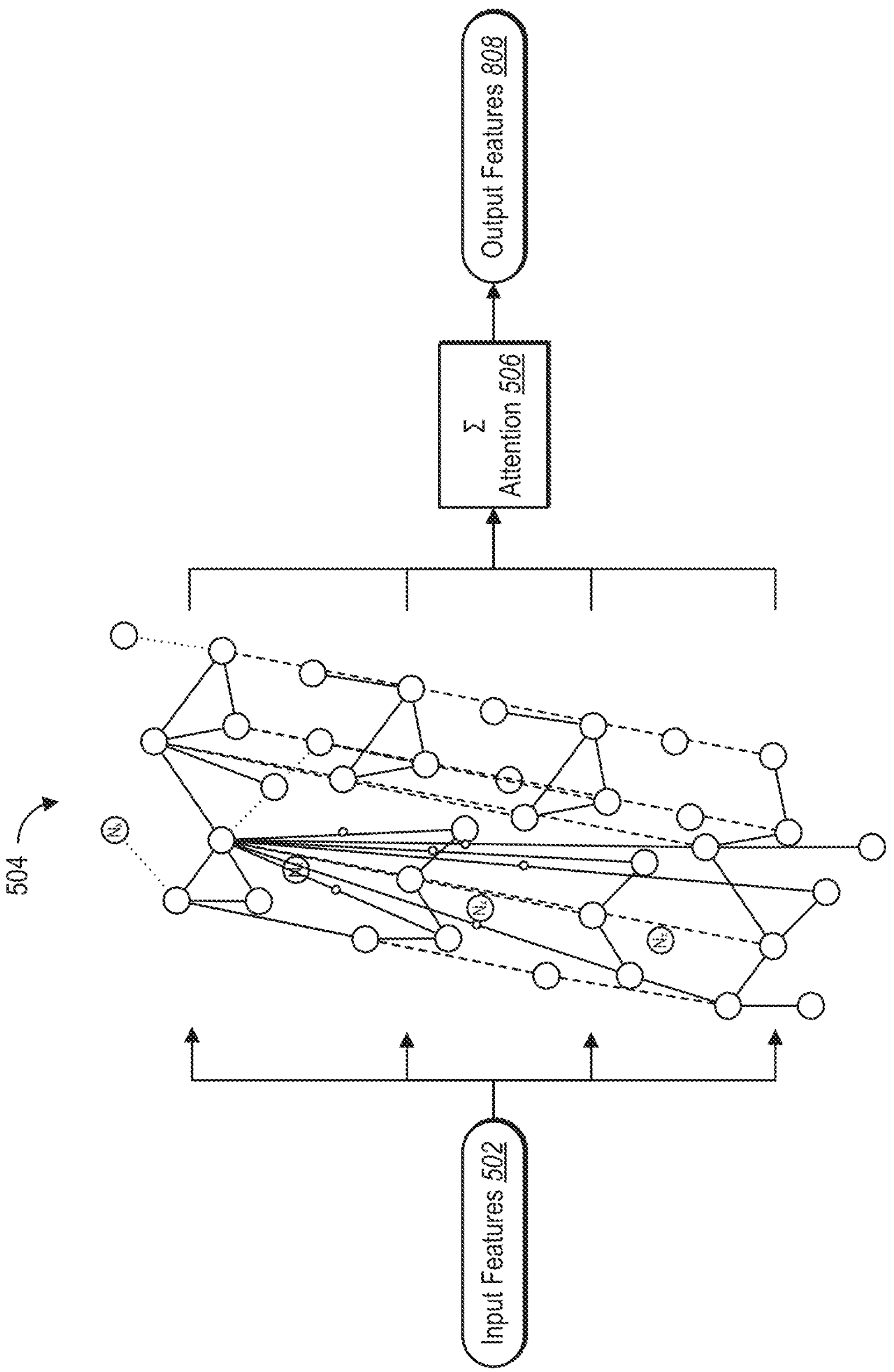
FIG. 5 illustrates utilizing a graph neural network and an attention model to generate perturbation features in accordance with one or more embodiments.

Further, as mentioned above, the latent transfer perturbation system can utilize a multilayer graph neural network as its perturbation neural network. FIG. 5 illustrates additional detail with regard to the process of utilizing the multilayer graph neural network. More specifically, FIG. 5 illustrates a process for utilizing a multilayer graph neural network in conjunction with an attention module.

As shown in FIG. 5, in one or more embodiments, the latent transfer perturbation system utilizes a multilayer graph neural network 504 to process input features 502. More specifically, in some embodiments, the latent transfer perturbation system provides input features 502 at each layer of the multilayer graph neural network 504. To illustrate, in some embodiments, the latent transfer perturbation system models each graph neural network layer as a non-linear function that learns the importance of neighbors via masked attention.

As also shown in FIG. 5, the latent transfer perturbation system utilizes an attention module 506 to determine output features 508. To illustrate, in one or more embodiments, the latent transfer perturbation system utilizes a graph neural network propagation rule to aggregate over node features both within layers and across layers of the multilayer graph neural network 504. Thus, the multilayer graph neural network 504 learns a low-dimensional latent representation for each node, including entity layer pairs. Accordingly, the latent transfer perturbation system can ensure that nodes that are similar within the multilayer graph neural network 504 have embeddings close to one another.

In one or more embodiments, the latent transfer perturbation system randomly initializes the input node features for each perturbation. Additionally, in one or more embodiments, the latent transfer perturbation system updates the features of node i in network-layer j for hidden layer k+1 using Formula (14) below:

$$h_{(i,j)}^{(k+1)} = o\left(\frac{1}{Q}\sum_{q=1\ \ldots\ Q}\left(\sum_{(j,m)\in\Gamma(i,j)\cup\psi(i,j)} \alpha_{(i,l)(j,m)}^{(q)} W^{(q,k)^T} h_{(j,m)}^{(q,k)}\right)\right) \quad (14)$$

Here, a is the normalized attention coefficient, q is the attention head, W is the learned weight matrix, h is the learned node features. In this setting, the latent transfer perturbation system averages the Q attention heads in order to improve the efficiency of usage of computing resources such as memory. Indices i, j correspond to the nodes, indices l, m to the corresponding layers, and q to the respective attention head.

In some embodiments, to account for the node links that are internal as well as external to a particular layer, the latent transfer perturbation system utilizes two functions, Γ and ψ, that for each pair entity-layer, return the neighbourhood of the entity that is internal and external to that layer, respectively. Formally, given an eitity $v_i$ in layer $L_l$, the set of within-layer neighbors are modeled by Formula (15) below:

$$\Gamma(i, l) = \{(j, l) \in V_{\mathcal{L}} \mid ((j, l),\ (i, j)) \in E_{\mathcal{L}}\} \quad (15)$$

Similarly, in one or more embodiments, the latent transfer perturbation system determines the set of outside-layer neighbors of $v_i$ in layers different from $L_l$ utilizing Formula (16) below:

$$\psi(i, l) = \{j, m) \in V_{\mathcal{L}} \mid (j, m),\ (i, j)) \in E_{\mathcal{L}},\ m \neq l\} \quad (16)$$

Figure 6:
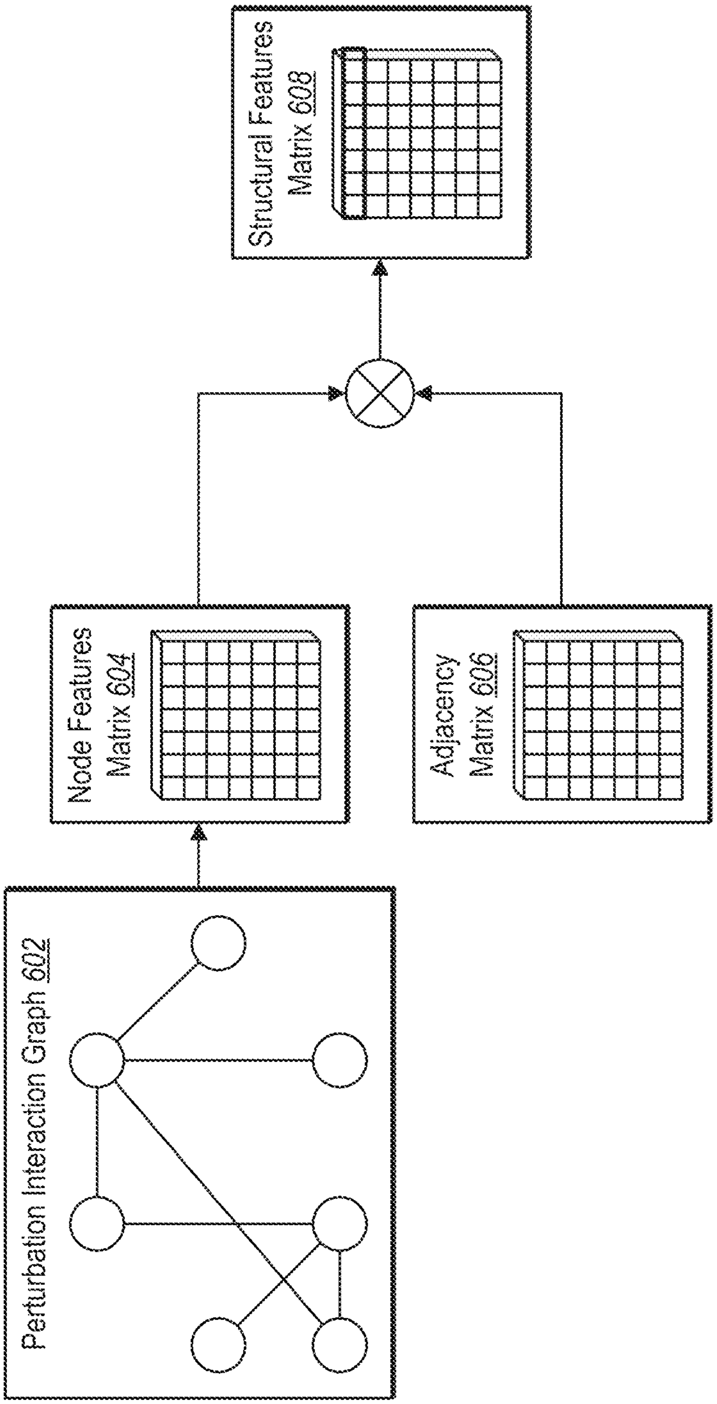
FIG. 6 illustrates utilizing a node features matrix and an adjacency matrix to generate a structural feature matrix in accordance with one or more embodiments.

Additionally, in one or more embodiments, the latent transfer perturbation system utilizes a perturbation neural network with a structural component. FIG. 6 illustrates this structural component of a perturbation neural network in accordance with one or more embodiments. In one or more embodiments, the latent transfer perturbation system learns a structural feature value of a node i through a structural feature generator $\mathcal{F}_\theta$.

To illustrate, as shown in FIG. 6, the latent transfer perturbation system utilizes a structural feature generator to analyze a perturbation interaction graph 602 and generate a node feature matrix 604 and an adjacency matrix 606. In one or more embodiments, the structural feature generator includes two multilayer perceptrons. Further, in one or more embodiments, the latent transfer perturbation system determines edge weights for the feature matrix 604 and the adjacency matrix 606.

Additionally, as shown in FIG. 6, the latent transfer perturbation system performs node feature aggregation to aggregate the node features from the feature matrix 604 and the adjacency matrix 606 and determine the structural features matrix 608. In one or more embodiments, the latent transfer perturbation system applies an additional neural network generate this structural features matrix 608 utilizing Formula (17) below:

$$x_i^{struct} = \mathcal{F}_\theta(A_i)\left(\sum\nolimits_{j \in N_i} - f_{\theta edge}(A_{ij})\right)$$

Accordingly, the structural features matrix 608 can differentiate between non-isomorphic graphs due to the structure-based node features. Accordingly, in one or more embodiments, the structural features matrix 608 improves the flexibility of the perturbation neural network.

Further, in one or more embodiments, the latent transfer perturbation system utilizes a graph transformer for the perturbation neural network. To illustrate, in some embodiments, the latent transfer perturbation system utilizes a sparse and efficient transformer architecture to reduce or eliminate excess computing costs incurred by dense self-attention mechanisms. Indeed, since dense self-attention mechanism leads to computational and memory costs that grow quadratically with the number of utilized tokens, the sparse transformer architecture yields significant efficiency improvements.

In one or more embodiments, the latent transfer perturbation system utilizes an expander graph as a perturbation modeler. In some embodiments, the latent transfer perturbation system utilizes the Exphormer model. In one or more embodiments, the latent transfer perturbation system builds a union graph by combining the edges of a multi-perturbation data object with edges from an expander graph. Accordingly, the latent transfer perturbation system can preserve the inductive bias of the multi-perturbation data object while improving information flow through shortcut paths and offering stronger theoretical guarantees.

More specifically, in one or more embodiments, the latent transfer perturbation system utilizes a model including a multi-head attention mechanism on a sparse attention pattern. Further, in some embodiments, the union graph includes the graph structure and an extender graph. With the sparse attention pattern denoted by $\mathcal{R}$, and $N_{\mathcal{R}}(i)$ denoting the set of neighbors for node i according to pattern $\mathcal{R}$, where $H=[h_1, \ldots, h_{N^*}]^\tau \in \mathbb{R}^{N^* \times d}$ is the matrix of node features from the previous layer, or initial node features, then the latent transfer perturbation system computes the updated feature vector for node i using t attention heads utilizing Formula (18) below:

$$ATTN_{\mathcal{R}}(H)_i := h_i + \sum_{j=1}^{t} V_i^J \sigma\left(\left(E_i^j \odot K_i^j\right)^T Q_i^j + B_i^j\right) \tag{18}$$

For Formula (18), $$Q_i^j = W_Q^j h_i$$

is the query vector derived from node i's features using projection matrix $$W_Q^j.$$

Additionally, for Forumla (14), $$K_i^j = W_K^j H_{N_{\mathcal{R}(i)}}^T$$

and $$V_i^j = W_V^j H_{N_{\mathcal{R}(i)}}^T$$

are the key and value matrices, respectively. They are computed by applying linear projections $$W_K^j$$

and $$W_V^j$$

to the features of the neighboring nodes $$H_{N_{\mathcal{R}(i)}}^T = [h_u]_{u \in N_{\mathcal{R}(i)}}^T.$$

Further, Edge features are incorporated via $$E_i^j = W_E^j \mathcal{E}_{N_{\mathcal{R}(i)}}$$

and $$B_i^j = W_B^j \mathcal{E}_{N_{\mathcal{R}(i)}}.$$

Here $$\varepsilon_{N_{\mathcal{R}(i)}} \in \mathbb{R}^{d_E} \times |N_{\mathcal{R}}(i)|$$

contains the features for edges connecting neighbors in $N_{\mathcal{R}}(i)$ to node i.

$$W_E^j$$

and $$W_B^j$$

are learnable projection matrices. The symbol ⊙ denotes element-wise multiplication, allowing edge features $$E_i^j$$

to modulate the keys $$K_i^j \cdot B_i^j$$

acts as an edge type attention bias term. Additionally, for Formula (14), σ represents the softmax function applied over the neighbors in $N_{\mathcal{R}}(i)$, calculating the attention weights. The expression $$V_i^j \sigma( \ldots )$$

computes the weighted sum of value vectors based on these attention weights for head j.

In some embodiments, the edge features are learnable embeddings are learnable embeddings specific to either expander edges or original edges of a knowledge graph, Accordingly, the latent transfer perturbation system can differentiate between information flowing along different types of connections within the attention pattern. Further, in one or more embodiments, each attention layer is followed by a node-wise feed-forward network with one hidden layer to create the output node features.

Further, to avoid potential duplication of sources caused by learnable embeddings, in one or more embodiments, the latent transfer perturbation system utilizes takes the union of all edges across the involved knowledge graphs and the expander graph. Indeed, rather than duplicating edges that appear in multiple sources, the latent transfer perturbation system encodes their provenance utilizing multi-hot edge features. In one or more embodiments, these features indicate which source graph each edge belongs to.

Mathematically, taking k source graphs with a shared set of nodes V and edge sets $E_1, E_2, \ldots E_k$, the latent transfer perturbation system constructs a unified graph with the node set V and an edge set defined by the union $E=E_1 \cup E_2 \cup \ldots \cup E_k$. For each edge $e \in E$, the latent transfer perturbation system defines a k-dimensional multi-hot feature vector $\varepsilon_e \in \{0,1\}^k$. The j-th component of this vector, denoted as $(\varepsilon_e)_j$, indicates membership in the j-th source graph according to Formula (19), below:

$$(\varepsilon_e)_j = \begin{cases} 1, & \text{if edge } e \in E_j \\ 0, & \text{otherwise.} \end{cases} \tag{19}$$

Thus, in one or more embodiments, the latent transfer perturbation system utilizes an Exphormer model variant in order to use multiple knowledge graphs simultaneously. The computational cost relates to the total number of unique edges in the union ($|E|=|E_1 \cup \ldots \cup E_k|$), which can be significantly less than the sum of edges across all graphs ($\Sigma|E_i|$) if there is substantial overlap, thus offering computational efficiency compared to processing graphs independently. Through these edge features (encoding provenance), the latent transfer perturbation system can effectively combine structural information from various knowledge graphs with the enhanced information propagation properties provided by the expander graph component.

In some embodiments, the latent transfer perturbation system combined learned node embeddings from a graph neural network and the structural component to learn prioritization of node embeddings. To illustrate, in one or more embodiments, the latent transfer perturbation system takes in the concatenated embeddings for learned perturbations from each layer of a graph neural network and determines a value between 0 and 1 for each embedding dimension with a sigmoid activation function. Further, in some embodiments, the latent transfer perturbation system utilizes separate transformation layers for each component in order to align features before combining. Further, to stabilize the layers, the latent transfer perturbation system can utilize a layer normalization function.

More specifically, in one or more embodiments, the latent transfer perturbation system gives each dimension its own gate value, allowing the model to selectively choose features utilizing Formula (20) below. Further, in some embodiments, the latent transfer perturbation system adds in residual connections and normalization to ensure that no information is lost during the transformation.

$$\text{combined} = z \times \text{struct\_transformed} + (1-z) \times \text{gnn\_transformed} \tag{20}$$

Figure 7:
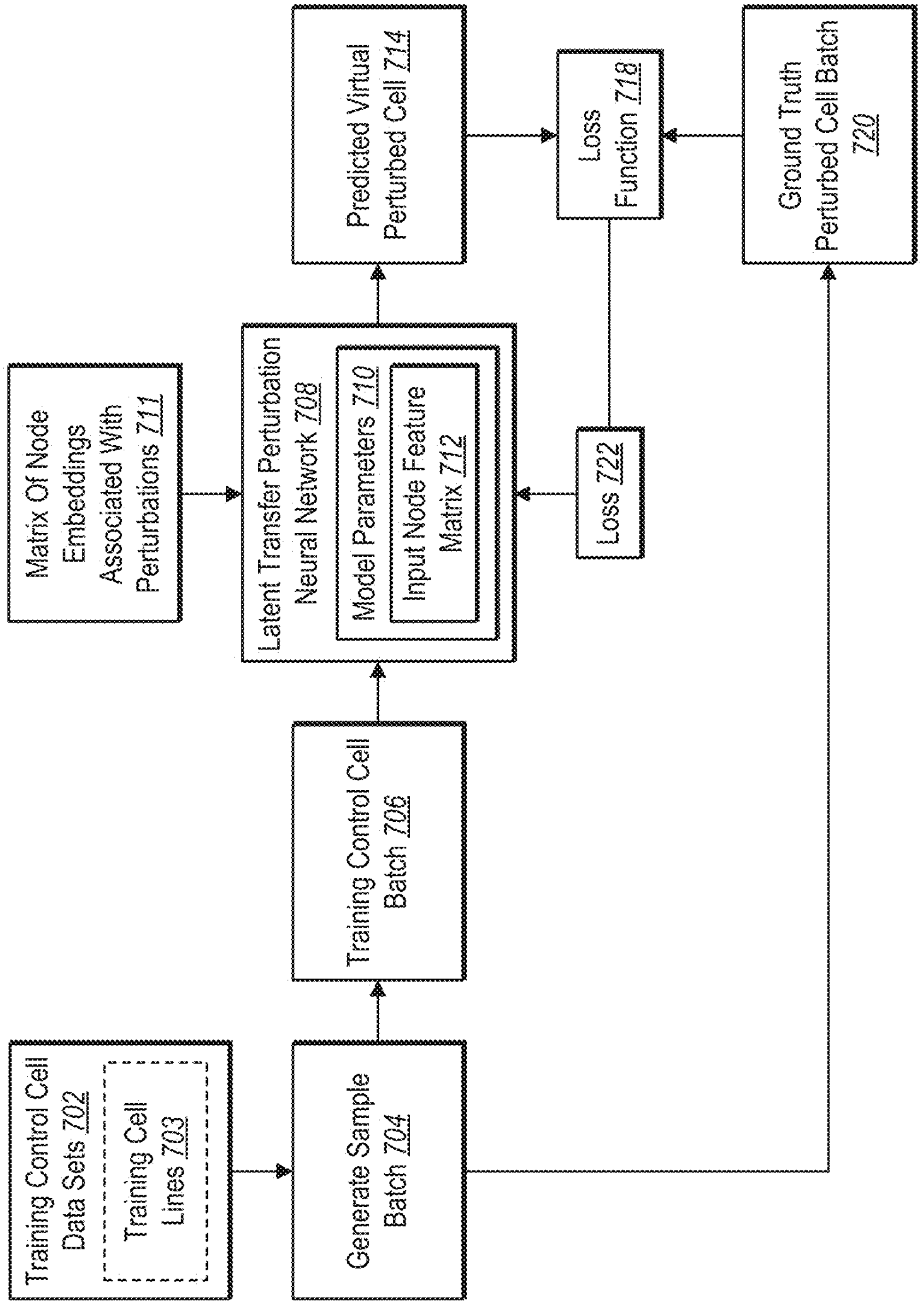
FIG. 7 illustrates a process for training a latent transfer perturbation neural network in accordance with one or more embodiments.

As mentioned above, in one or more embodiments, the latent transfer perturbation system trains the latent transfer perturbation neural network to generate virtual perturbed cells including virtual perturbed cell response features. FIG. 7 illustrates a pipeline for training the latent transfer perturbation neural network in accordance with one or more embodiments. As shown in FIG. 7, the latent transfer perturbation system utilizes training control cell datasets 702 to train the latent transfer perturbation neural network. In some embodiments, the training control cell datasets 702 include training cell lines 703. Any of the training cell lines 703 utilized to train the latent transfer perturbation neural network are seen or in-distribution.

In one or more embodiments, as shown in FIG. 7, the latent transfer perturbation system can utilize the training control cell datasets 702 to perform an act 704 of generating a sample batch. More specifically, the latent transfer perturbation system utilizes the training control cell datasets 702 to generate a training control cell batch 706 and a corresponding ground truth perturbed cell batch 720. To illustrate, the latent transfer perturbation system samples a batch of perturbed cell profiles and samples corresponding ground-truth control cells from the same experimental batches.

Further, as shown in FIG. 7, the latent transfer perturbation system provides the training control cell bath 706 to a latent transfer perturbation neural network 708 including model parameters 710, which include an input node feature matrix 712. As also shown in FIG. 7, the latent transfer perturbation neural network 708 also receives a matrix of node embeddings associated with perturbations 711. Indeed, in one or more embodiments, the latent transfer perturbation system generates the input node feature matrix 712 based on the matrix of node embeddings associated with perturbations. For example, $z_p \in \mathbb{R}^d$ required for the latent shift is the p-th row of Z. More specifically, in this example, the perturbation neural network 110 associated each perturba tion $P \in \{1, \ldots, N\}$ with a randomly initialized node embedding $$h_p^0 \in \mathbb{R}^{d_0}, d_0 \in \mathbb{N}$$

that are consolidated in the input node feature matrix 712, as $H^0 \in \mathbb{R}^{N \times d_0}$.

As shown in FIG. 7, the latent transfer perturbation neural network 708 generates a predicted virtual perturbed cell 714 based on a control cell from the training control cell batch 706. Further, the latent transfer perturbation system compares the predicted virtual perturbed cell 714 to a ground-truth cell from the ground-truth perturbed cell batch 720 utilizing a loss function 718. Additionally, as shown in FIG. 7, the latent transfer perturbation system determines a loss 722 and utilizes the loss 722 to modify the model parameters 710, including the input node feature matrix 712.

In some embodiments, during training, the latent transfer perturbation system treats the input node feature matrix 712 as model parameters that are learned backpropagation. Further, in one or more embodiments, the latent transfer perturbation system refines the input node feature matrix 712 utilizing a graph attention transformer model for message passing of an L-layer graph neural network within the perturbation neural network of the latent transfer perturbation system. For example, via Formula (21) below:

$$H^{\ell} = LAYER_{\theta\ell}(H_{\ell-1}), \; 0 \leq \ell \leq L \tag{21}$$

This backpropagation including the input node feature matrix 712 that allows the model to characterize perturbation effects from various multi-perturbation data objects (e.g. biological knowledge graphs). Accordingly, the latent transfer perturbation system can perform a plurality of training cycles until the loss 722 is sufficiently minimized and the model parameters 710, including the input node feature matrix 712 are sufficiently optimized. To illustrate, the latent transfer perturbation neural network can utilize the following training algorithm:

Require: Pert. cells y, control cells x, biological prior graph $G=(V,E)$ with perturbations $P \subset V$ Ensure: Minimize MSE loss between predicted and true perturbed cell measurements 1: Initialize input perturbation embeddings $$\{h_v^0\}_{v \in V}$$

randomly

2: for each training step do

3: Sample a batch of perturbed cell profiles:

$$\{y_i\}_{i=1}^{B} \subset y$$

4: Sample corresponding control cells from the same experimental batches:

$$\{x_i\}_{i=1}^{B} \subset x$$

5: Enrich perturbation embeddings using graph prior:

$$\{z_v\}_{v \in V} \leftarrow GNN\left(G, \{h_v^0\}_{v \in V}\right)$$

6: for each sample in batch do

7: Encode control cells into basal latent space: $b_i \leftarrow MLP_{basal}(x_i)$ 8: Retrieve perturbations $P_i \subset P$ associated to target $y_i$ 9: Combine control and perturbation embeddings: $\hat{z}_i \leftarrow COM(b_i, \{z_p : p \in P_i\})$ 10: Decode to predicted perturbed profile: $\hat{y}_i \leftarrow MLP_{dec}(\hat{z}_1)$ 11: Compute loss for each sample: $\mathcal{L}_1 \leftarrow MSE(\hat{y}_i, y_i)$ 12: end for 13: Compute total loss over batch:

$$\mathcal{L}_1 \leftarrow \sum_{i=1}^{B} \mathcal{L}_i$$

14: Backpropagate and update model parameters

15: end for

Figure 8:
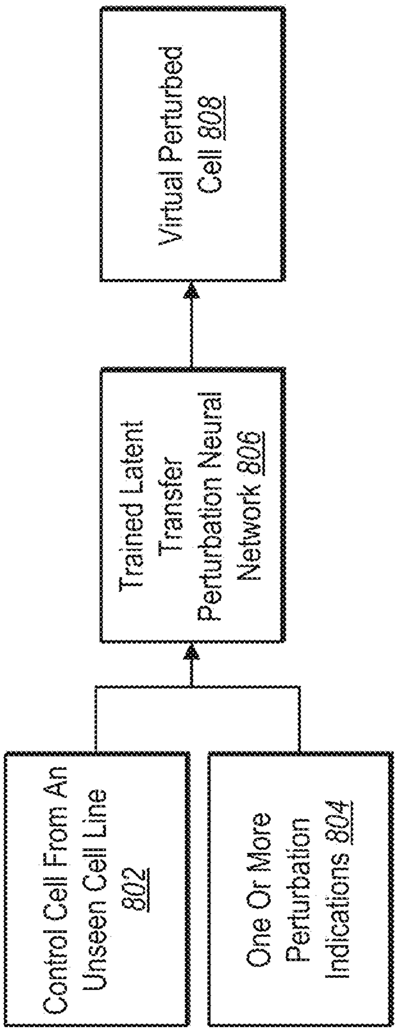
FIG. 8 illustrates a process for utilizing a latent transfer perturbation neural network for out-of-distribution cell lines in accordance with one or more embodiments.

As mentioned above, the latent transfer perturbation system can accurately determine virtual perturbed cells for both in-distribution and out-of-distribution cell lines. FIG. 8 illustrates a process for utilizing the latent transfer perturbation neural network to generate a virtual perturbed cell to an unseen cell line. Further, as will be discussed below with regard to FIG. 10B, the latent transfer perturbation neural network maintains accurate performance for unseen cell lines.

As shown in FIG. 8, in one or more embodiments, the latent transfer perturbation system provides a control cell from an unseen cell line 802 and one or more perturbation indications 804 to a trained latent transfer perturbation neural network 806. In one or more embodiments, an unseen cell line is any cell line that the trained latent transfer perturbation neural network 806 was not directly trained with. An unseen cell line can also be referred to as an out-of-distribution cell line. As shown in FIG. 8, in one or more embodiments, the trained latent transfer perturbation neural network 806 generates a virtual perturbed cell 808. As mentioned above, and as will be discussed below with regard to FIG. 10B, the trained latent transfer perturbation neural network 806 can accurately generate the virtual perturbed cell 808 despite not having any training associated with the control cell from the unseen cell line 802.

Figure 9:
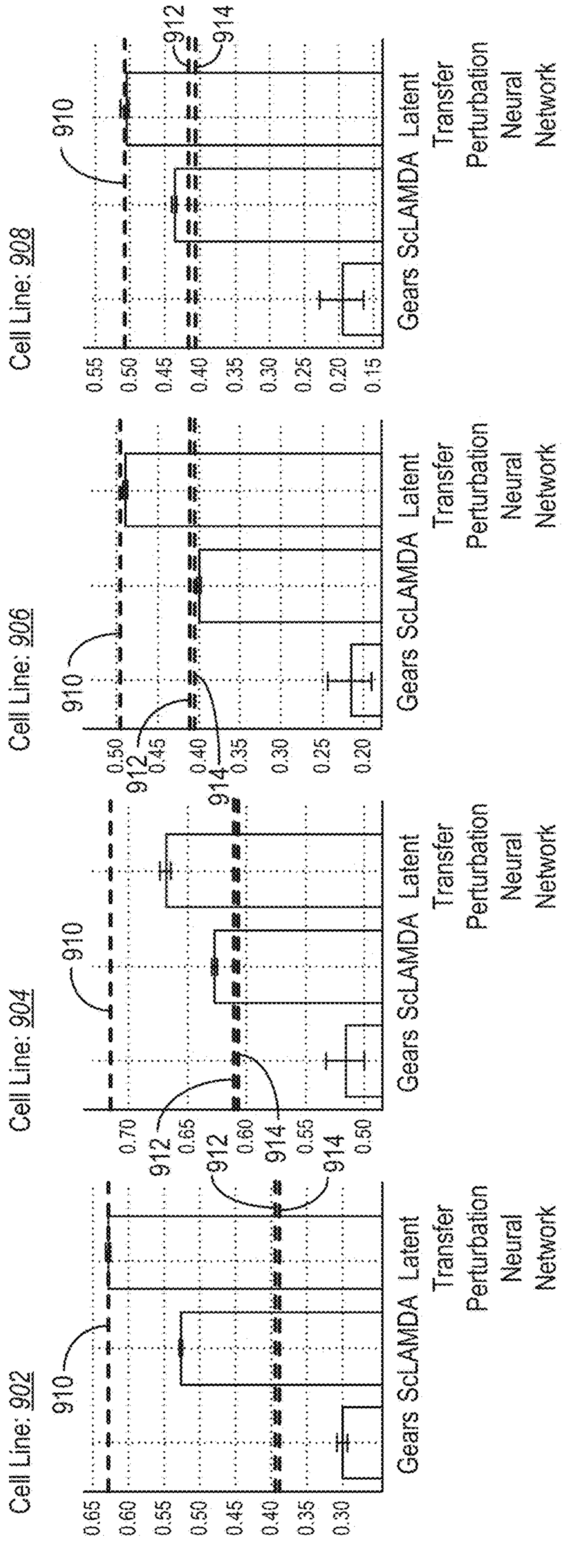
FIG. 9 illustrates improved performance of the latent transfer perturbation neural network compared to other neural networks on predicting unseen single perturbations within a known cell type.

FIGS. 9-11 relate to evaluation of the latent transfer perturbation neural network relative to other neural networks. As mentioned above, conventional perturbation prediction systems have significant problems with accuracy. Further, the evaluation of predicted virtual perturbed cells has a variety of problems and shortcomings. Indeed, the modeling of predicted transcriptomic cell profiles after a perturbation is a new field with many open questions and an absence of clear consensus for the best practices for evaluation. Notably, experimental batch effects are a significant challenge to evaluating predicted virtual perturbed cells.

Experimental batch effects in evaluating predicted virtual perturbed cells are a significant problem in part because absolute values vary drastically in biological data due to the sensitivity and variability of biological systems and their interaction with environments. To account for this variability, some studies include designed controls in every match. However, many deep learning models rely on a global control mean to compute perturbation effects. In a scenario where batch effects are present and any confounding between batch and applied perturbation occurs, failure to account for the batch effects can result in mistaking background batch-wise variance for perturbation effect and overestimating model performance, reduce true performance by adding avoidable noise, or both. Indeed, analyzing genome-wide datasets and quantifying control-control correlations both within and across batches confirms substantial batch effects. To illustrate, across-batch correlations are significantly lower despite involving more aggregated cells.

Further, there are significant confounding effects between batch and perturbation in conventional models. Indeed, as a library of perturbants is applied to pooled cells in genome-wide datasets, there are significant association between batch and perturbation identifiers across these datasets. This confirms significant batch effects and confounding between perturbation identity and batch assignment. Consequently, the data provided in FIGS. 9-11 adopts batch-matched controls for model evaluation to maintain biological validity and to reduce noise.

Further, because mean-baseline models have strong predictive performance, evaluating models purely based on mean perturbation response is insufficient for assessing their capacity to distinguish between biologically distinct perturbations. Indeed, the strong predictive power of the mean baseline is a feature of the data that reflects general biological responses to perturbation-induced stress or a reduction in fitness, health, or growth due to perturbation of an important cellular component, rather than perturbation-specific effects. Accordingly, the data provided in FIGS. 9-11 adopts a complementary evaluation approach using retrieval metrics, which explicitly measure how effectively a model distinguishes replicate perturbations from other perturbations. More specifically, the data related to evaluation of neural networks provided in FIGS. 9-11 utilizes cosine similarity and Pearson correlation applied directly to delta profiles. Indeed, evaluation of neural networks the data related to evaluation of neural networks provided in FIGS. 9-11 utilizes Pearson Δ as the primary evaluation metric, complemented by retrieval scores during final testing to holistically assess perturbation-specific signal retention.

For the data provided in FIGS. 9-11, the data was split into train, validation, and test sets via grouping by perturbation such that distinct sets of unseen perturbations were reserved both for the validation sets and test sets with a target ration of 0.5625, 0.1875, and 0.25, for train, validation and test, respectively. Moreover, for the cross cell type task, the test set was a reserved cell type with only control cells included during training with a breakdown into seen and unseen perturbations therein. As an exception, for the doubles task on the Norman dataset pre-defined splits were loaded from the GEARS setup. Optimal hyperparameters for each model were selected based on the validation Pearson Δ metric. Only metrics on the test set are reported.

For the data provided with regard to FIGS. 9-11, all metrics are reported as weighted averages, i.e., the mean of the mean across cells subjected to each unique perturbation, unless otherwise specified. Further, expression values $x \in X \cup Y$, are represented as a Log1p-transformed and library size-normalized counts, with target library size 4,000. For example, for a raw count $x_{raw} \in \mathbb{R}^n$, data from FIGS. 9-11 can utilize Formula (22) below:

$$x := \log\left(1 + 4000 \cdot \frac{x_{raw}}{\|x_{raw}\|_1}\right) \tag{22}$$

Further, with regard to a delta representation, which is centered on batch-matched controls, for each perturbed cell expression $\delta_i := y_i - \bar{x}_{c,b}$, with cell line c and batch b and where $\bar{x}_{c,b}$, represents the mean expression of control cells $x \in X$, the latent transfer perturbation system can utilize Formula (23) below:

$$\delta_i := y_i - \bar{x}_{c,b}, \tag{23}$$

The data in FIGS. 9-11 utilizes Pearson Δ slightly modified from the metric Pearson Correlation or Delta Expression. More specifically, Pearson Δ calculates the correlation between predicted and observed log fold change versus batch-match control mean as Formula (24) below, where $\hat{\delta}_p$, and $\delta_p$ are the batch-matched control centering of the prediction and ground truth, respectively, averaged across replicates of certain perturbation $p \in P$.[4] The results across all predicted perturbation effects are then averaged to obtain an overall performance estimate.

$$\text{PEARSON}\Delta(p) := \text{PEARSON}(\hat{\delta}_p, \delta_p) \tag{24}$$

For the GEARS model only, the graphs below in FIGS. 9-11 report the exact "Pearson Correlation (Delta Expression)" from the GEARS code base instead. Indeed, any differences between "Pearson Correlation (Delta Expression)" and our "Pearson Δ" are much smaller in practice than the differences between models.

For retrieval, the data reported in FIGS. 9-11 utilizes two variants of the retrieval rank metric that score a prediction's similarity to the ground truth not overall, but relative to other perturbations. These metrics are the same as RankAverage from PerturBench, but focus on similarity with a perfect score of 1, a random score of 0.5, and perfect anti-correlated prediction score of 0, according to the following Formula (25) below:

$$\text{RETRIEVAL}(p) := \frac{1}{N}\sum_{p \in P} \text{rank}(\hat{\delta}_p), \tag{25}$$

$$\text{rank}(\hat{\delta}_p) := \frac{1}{N-1}\sum_{\substack{q \in P \\ q \neq p}} 1_{\{PEARSON(\hat{\delta}_p, \delta_p) \geq PEARSON(\hat{\delta}_p, \delta_q)\}}$$

For "normalized" retrieval the perturbation count $N := |P|$ matches the original experiment, whereas for "fast retrieval" for computational efficiency a seeded random reference set of only 100 perturbations is used, with the addition of the query perturbant p when not in the reference set, so $N \in \{100, 101\}$. Similar to Person A, the data below in FIGS. 9-11 report averaged performance across all perturbations.

With regard to the non-learned general baseline reported for FIGS. 9-11, the performance floor reflects a non-learned general baseline model that predicts expression profiles using mean values observed in the training data. This baseline uses an additive approach that combines (1) the mean test cell type control expression profile, (2) either the perturbation-specific mean changes for seen perturbations or the global perturbation mean for unseen perturbations, and (3) a weighted average according to the number of samples per cell line if multiple cell lines are present in a training set.

With regard to training models for the data in FIGS. 9-11, consider a multi-set of training samples TRAIN $\subset P_{train} \times$ $C_{train} \times B_{train}$ consisting of combinations of perturbation(s), cell line and batch effect with a test multi-set TEST defined analogously. Consider a perturbation p so that $(p, c_p, b_p) \in$ TEST with cell line cp and batch effect bp. Implicitly, $(c_p, b_p)$ map to a set of control cell profiles associated to that context. Thus, for $(p, c, b) \in$ TRAIN, then Formula (26) below:

$$\hat{y}_{(p,c_p,b_p)} = \bar{x}_{(c_p,b_p)} + \frac{1}{|(q, c, b) \in \text{TRAIN} : q = p|} \sum_{\substack{(q,c,b) \in \text{TRAIN} \\ q=p}} y_{(p,c,b)} - \bar{x}_{(c,b)} \tag{26}$$

Otherwise, use the global delta across perturbations observed in TRAIN, as in Formula (27), below:

$$\hat{y}_{(p,c_p,b_p)} = \bar{x}_{(c_p,b_p)} + \frac{1}{|\text{TRAIN}|} \sum_{(q,c,b) \in \text{TRAIN}} y_{(p,c,b)} - \bar{x}_{(c,b)} \tag{27}$$

For the data presented below with regard to FIGS. 9-11 with multi-perturbations, this baseline is implemented to initially attempt to use samples where the exact perturbation configuration is present. Otherwise, the perturbation is split into its components and each component is sequentially added to the test control mean according to the above method, adding a local delta estimate if available and resorting to a global delta otherwise.

With regard to experimental reproducibility estimates referenced with regard to FIGS. 9-11, the experimental reproducibility estimates utilize a focus on distribution means with a split-half validation approach. More specifically, for each combination of perturbations, cell line context, and batch, the experimental reproducibility estimates are determined based on dividing test cells into two roughly equal halves, calculating mean expression profiles for each half, and measuring the agreement between these means.

To account for the randomness in choosing the half-split, the experimental reproducibility estimates reflect repeats in the experiment across multiple seeded runs and report average performance. This provides a performance benchmark analogous to human-level reproducibility, which is called accuracy in other machine learning domains.

Thus, for a set of expression profiles $S \subset Y$ for a fixed perturbation cell line context and batch (p, c, b), where METRIC represents any evaluation metric including Pearson Δ, RETRIEVAL, or MSE, experimental reproducibility utilizes the following Algorithm:

$$S' \subseteq S: |S'| \approx |S|/2$$

$$\bar{S}_1 = \frac{1}{|S'|} \sum_{y \in S'} y$$

$$\bar{S}_2 = \frac{1}{|S \backslash S'|} \sum_{y \in S \backslash S'} y$$

then report, REPRODUCE(p, c, b)=METRICS($\bar{S}_1$,$\bar{S}_2$)

FIG. 9 illustrates a graph showing the performance of the latent transfer perturbation neural network compared to two notable perturbation prediction models: graph-enhanced gene activation and repression simulator (GEARS) and ScLAMDA. More specifically, FIG. 9 illustrates the performance on predicting unseen (out-of-distribution) single perturbations within a known cell type. The bottom horizontal bar 910 represents a general baseline. The middle horizontal bar 912 represents a batch-informed model capturing potential compounding. The top horizontal bar 914 represents experimental reproducibility.

Cell line 902 is a myelogenous leukemia lymphoblast cell line. As shown in FIG. 9, for the cell line 902, GEARS shows a Pearson Δ of approximately 0.30 and ScLAMDA shows a Pearson Δ of approximately 0.525. As shown in FIG. 9, the latent transfer perturbation neural network shows a Pearson Δ of approximately 0.625.

Further, cell line 904 is a retinal pigment epithelial cell line. For the cell line 904, GEARS shows a Pearson Δ of approximately 0.520 and ScLAMDA shows a Pearson Δ of approximately 0.625. As shown in FIG. 9, the latent transfer perturbation neural network shows a Pearson Δ of approximately 0.670.

Additionally, cell line 906 is a liver hepatocellular carcinoma cell line. For the cell line 906, GEARS shows a Pearson Δ of approximately 0.20 and ScLAMDA shows a Pearson Δ of approximately 0.39. As shown in FIG. 9, the latent transfer perturbation neural network shows a Pearson Δ of approximately 0.49.

Cell line 908 is a human T lymphocytes cell line. For the cell line 908, GEARS shows a Pearson Δ of approximately 0.19 and ScLAMDA shows a Pearson Δ of approximately 0.44. As shown in FIG. 9, the latent transfer perturbation neural network shows a Pearson Δ of approximately 0.51. Accordingly, the latent transfer perturbation neural network shows significantly more accurate generation of virtual cell perturbation effects relative to GEARS and ScLAMDA for all of the cell lines 902-908.

Figure 10B:
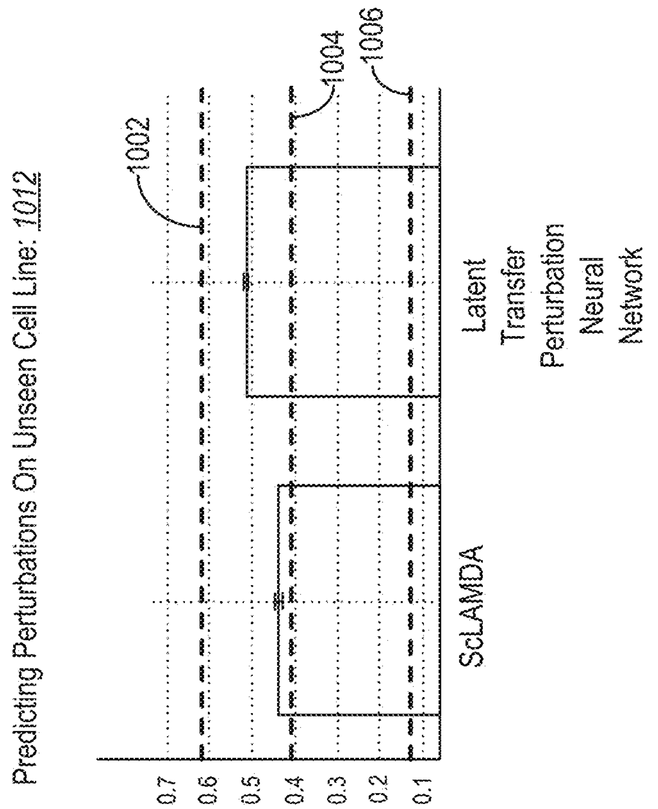
FIGS. 10A-10B illustrates improved performance of the latent transfer perturbation neural network compared to other neural networks on predicting unseen single perturbations within a known cell type.
Figure 10A:
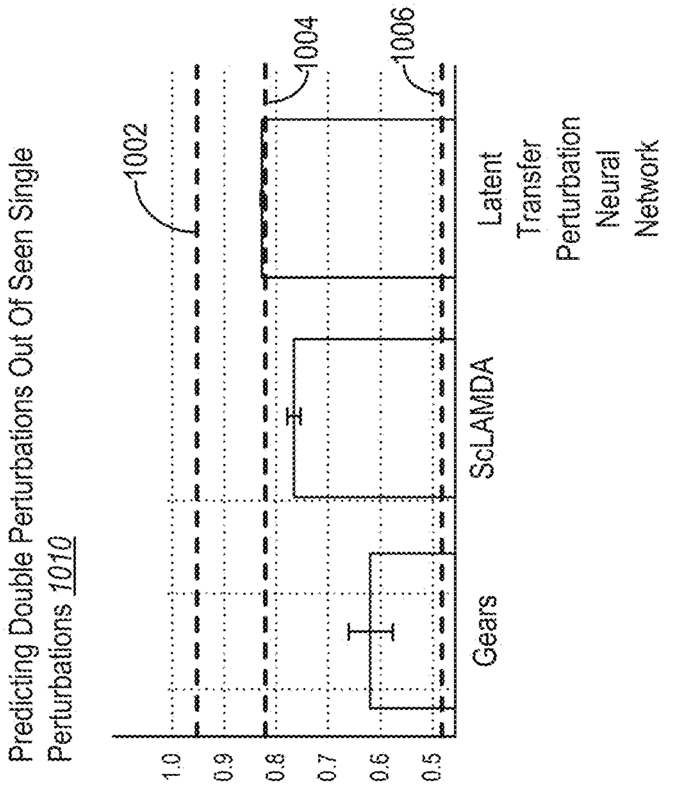

FIGS. 10A-10B illustrate further performance evaluation of the latent transfer perturbation neural network compared to GEARS and ScLAMDA. As mentioned above with regard to FIG. 9, the bottom horizontal bar 1002 represents a general baseline. Additionally, the middle horizontal bar 1004 represents a batch-informed model capturing potential compounding, and the top horizontal bar 1006 represents experimental reproducibility.

In FIG. 10A, graph 1010 illustrates the performance of the latent transfer perturbation neural network, GEARS, and ScLAMDA in predicting double perturbation effects from trained single perturbations. As shown in FIG. 10A, GEARS shows a Pearson Δ of approximately 0.61. Additionally, ScLAMDA shows a Pearson Δ of approximately 0.75. Further, the latent transfer perturbation neural network shows a Pearson Δ of approximately 0.82. Accordingly, the latent transfer perturbation neural network also outperforms GEARS and ScLAMDA in predicting double perturbations from trained single perturbations.

In FIG. 10B, graph 1012 illustrates the performance of the latent transfer perturbation neural network and ScLAMDA in predicting single perturbations in a variety of unseen (out-of-distribution) cell lines. The data for FIG. 10B was assessed through four leave-one-out experiments, with all perturbation examples from the target cell line are held out, but the neural networks are trained on all other controls. As shown in FIG. 10B, ScLAMDA shows a Pearson Δ of approximately 0.45. However, the latent transfer perturbation neural network shows a Pearson Δ of approximately 0.51. Thus, the latent transfer perturbation neural network also outperforms ScLAMDA at predicting virtual perturbations for out-of-distribution cell lines.

FIG. 11 illustrates the results of an ablation study for the latent transfer perturbation neural network on an unseen cell line. More specifically, FIG. 11 illustrates Pearson Δ values for performance on unseen cell lines. To illustrate, FIG. 11 shows performance for various configurations including the latent transfer perturbation neural network with no basal encoder 1102, the latent transfer perturbation neural network with multilayer perceptron 1104, and the latent transfer perturbation neural network with transcriptomic embeddings and the multilayer perceptron 1106. Further, FIG. 11 illustrates the performance of these configurations for standard 1108, no basal matching 1110, no basal averaging 1112, and no basal matching or averaging 1114.

As shown in FIG. 11, the latent transfer perturbation neural network with no basal encoder 1102 has a standard 1108 value of 0.469, a no basal matching 1110 value of 0.413, a no basal averaging 1112 value of 0.468, and a no basal matching or averaging 1114 value of 0.413. Additionally, as shown in FIG. 11, the latent transfer perturbation neural network with multilayer perceptron 1104 has a standard 1108 value of 0.443, a no basal matching 1110 value of 0.451, a no basal averaging 1112 value of 0.428, and a no basal matching or averaging 1114 value of 0.446. As also shown in FIG. 11, the latent transfer perturbation neural network with transcriptomic embeddings and the multilayer perceptron 1106 has a standard 1108 value of 0.440, a no basal matching 1110 value of 0.448, a no basal averaging 1112 value of 0.468, and a no basal matching or averaging 1114 value of 0.443.

With respect to basal matching and averaging, both consistently lead to improved experimental results and are part of the standard configuration of the latent transfer perturbation neural network. While the basal matching mitigates undesired discrepancies between cells subject to different batch effects, control averaging synergizes well with the training and evaluation methodology that aims to predict the mean perturbation effect across samples subject to the same perturbation, for example, by optimizing mean squared error and calculating metrics aggregated across samples on the perturbation level.

Figure 12:
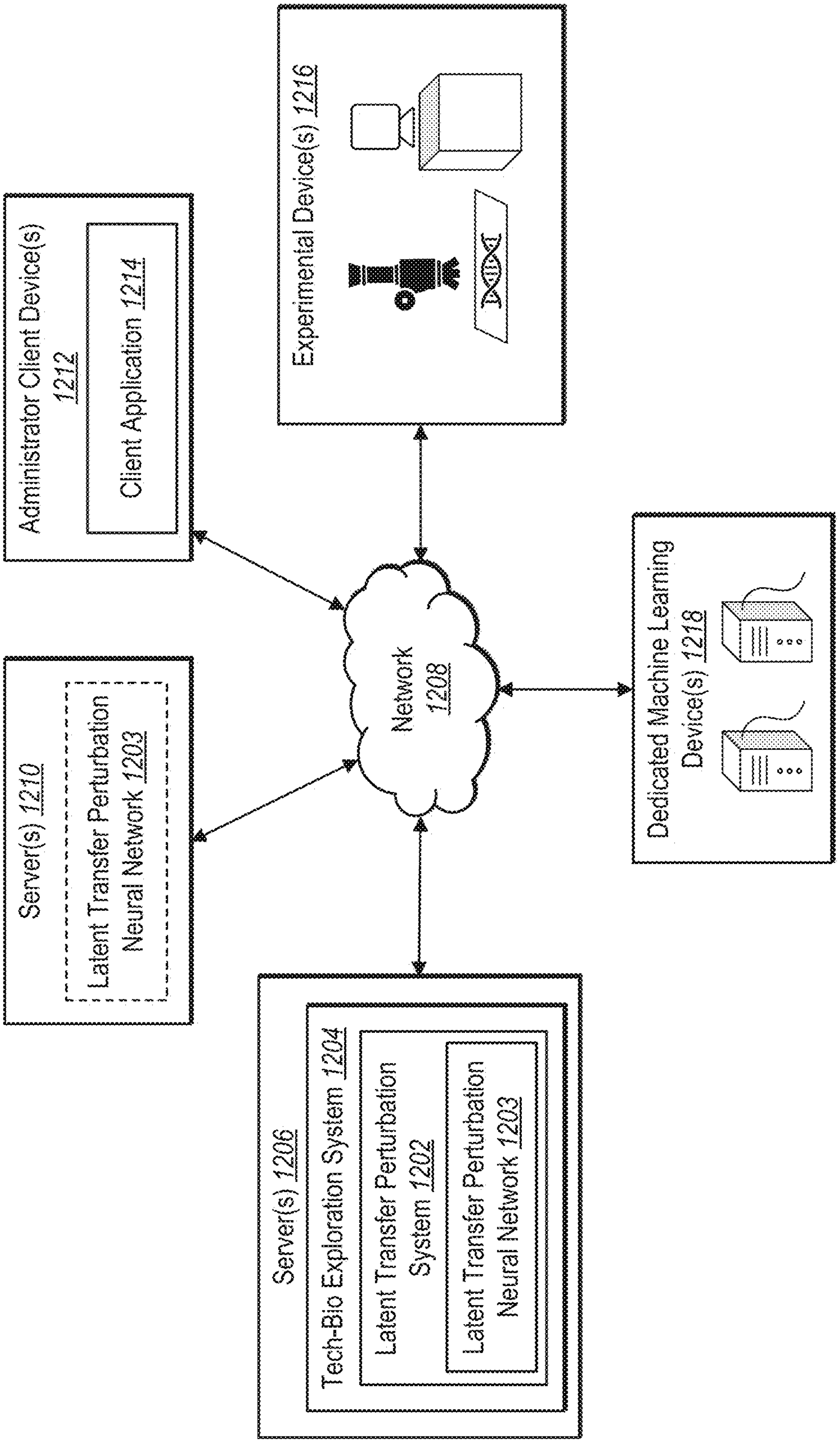
FIG. 12 illustrates a diagram of an environment in which a latent transfer perturbation system can operate in accordance with one or more embodiments.

Additional detail regarding the computing environment in which a latent transfer perturbation system 1202 (e.g., the latent transfer perturbation system described above) operates will now be provided with reference to FIG. 12. In particular, FIG. 12 illustrates a schematic diagram of a system environment in which the latent transfer perturbation system 1202 can operate in accordance with one or more embodiments.

As shown in FIG. 12, the environment includes server(s) 1206 (which includes a tech-bio exploration system 1204 and the latent transfer perturbation system 1202), administrator client device(s) 1212, and a network 1208. As further illustrated in FIG. 12, the various computing devices within the environment can communicate via the network 1208. Although FIG. 12 illustrates the latent transfer perturbation system 1202 being implemented by a particular component and/or device within the environment, the latent transfer perturbation system 1202 can be implemented—in whole or in part—by other computing devices and/or components in the environment (e.g., additional client device(s)). Additional description regarding the illustrated computing devices is provided with respect to FIG. 14 below.

As shown in FIG. 12, the server(s) 1206 (e.g., one or more local servers operated by a particular entity) can include the tech-bio exploration system 1204. In some embodiments, the tech-bio exploration system 1204 can determine, store, generate, and/or provide for display tech-bio information including maps of biology, experiments from various sources, and/or machine learning tech-bio predictions. For instance, the tech-bio exploration system 1204 can analyze data signals corresponding to various treatments or interventions (e.g., compounds or biologics) and the corresponding relationships in genetics, proteomics, phenomics (e.g., cellular phenotypes), and invivomics (e.g., expressions or results within a living animal). Moreover, the tech-bio exploration system 1204 provides an environment for operating, executing, and/or managing complex drug discovery pipelines.

For instance, the tech-bio exploration system 1204 can generate and access experimental results corresponding to gene sequences, protein shapes/folding, protein/compound interactions, phenotypes resulting from various interventions or perturbations (e.g., gene knockout sequences or compound treatments), and/or in vivo experimentation on various treatments in living animals. By analyzing these signals (e.g., utilizing various machine learning models), the tech-bio exploration system 1204 can generate or determine a variety of predictions and inter-relationships for improving treatments/interventions.

To illustrate, the tech-bio exploration system 1204 can generate maps of biology indicating biological inter-relationships or similarities between these various input signals to discover potential new treatments as part of the complex compound discovery process. For example, the tech-bio exploration system 1204 can utilize machine learning and/or maps of biology to identify a similarity between a first gene associated with disease treatment and a second gene previously unassociated with the disease based on a similarity in resulting phenotypes from gene knockout experiments. The tech-bio exploration system 1204 can then identify new treatments based on the gene similarity (e.g., by targeting compounds the impact the second gene). Similarly, the tech-bio exploration system 1204 can analyze signals from a variety of sources (e.g., protein interactions, in vivo experiments) to predict efficacious treatments based on various levels of biological data.

The tech-bio exploration system 1204 can generate graphical user interfaces to convey tech-bio information and receive user input for intelligently exploring tech-bio information. Indeed, as mentioned above, the tech-bio exploration system 1204 can generate graphical user interfaces displaying different maps of biology that intuitively and efficiently express complex interactions between different biological systems for identifying improved treatment solutions. Furthermore, the tech-bio exploration system 1204 can also electronically communicate tech-bio information between various computing devices.

The tech-bio exploration system 1204 can include a system that facilitates various models or algorithms for generating maps of biology (e.g., maps or visualizations illustrating similarities or relationships between genes, proteins, diseases, compounds, and/or treatments) and discovering new treatment options over one or more networks. For example, the tech-bio exploration system 1204 collects, manages, and transmits data across a variety of different entities, accounts, and devices. In some cases, the tech-bio exploration system 1204 is a network system that facilitates access to (and analysis of) tech-bio information within a centralized operating system. Indeed, the tech-bio exploration system 1204 can link data from different network-based research institutions to generate and analyze maps of biology.

As shown in FIG. 12, the tech-bio exploration system 1204 can include the latent transfer perturbation system 1202 that generates, stores, manages, and transmits data pertaining to virtual perturbations and virtual perturbed cells. For example, in the context of the above description for the tech-bio exploration system 1204, in some embodiments, the tech-bio exploration system 1204 further utilizes the latent transfer perturbation system 1202 to enhance the coordination between various groups involved in the drug discovery process. For instance, the latent transfer perturbation system 1202 works in tandem with the tech-bio exploration system 1204 to generate virtual perturbed cells, transmit the virtual perturbed cells to one or more devices, and initiate one or more downstream model predictions or processes based on the virtual perturbed cells.

As also shown in FIG. 12, the latent transfer perturbation system 1202 includes a latent transfer perturbation neural network 1203. As discussed above, the latent transfer perturbation system 1202, and by extension the tech-bio exploration system 1204, can utilize the latent transfer perturbation neural network 1203 to generate virtual perturbed cells. Therefore, the tech-bio exploration system 1204 is able to utilize the generated virtual perturbed cells for prediction, data collection, and other tasks.

As also illustrated in FIG. 12, the environment includes the administrator client device(s) 1212. As mentioned above, the administrator client device(s) 1212 can be involved in the process of drug discovery. Thus, for example, the administrator client device(s) 1212 can coordinate/manage virtual perturbations, including input control cell(s) and perturbation(s). Moreover, the administrator client device(s) 1212 can coordinate/manage a second stage such as generating a report or other communication based on a virtual perturbed cell. Further, the administrator client device(s) 1212 can coordinate/manage a third stage of utilizing the bioactivity prediction to generate one or more additional predictions or initiate one or more programs (IPG or ICG).

To illustrate, the administrator client device(s) 1212 can include computing devices that implement or manage a compound program generation stage of a compound discovery process. Similarly, the administrator client device(s) 1212 can include computing devices that implement or manage a compound lead generation stage and the administrator client device(s) 1212 can include computing devices that implement or manage a compound/dose selection stage. For example, the latent transfer perturbation system 1202 can receive one or more requests to utilize the latent transfer perturbation neural network 1203 to generate one or more phenomic virtual perturbed cells. For instance, the latent transfer perturbation system 1202 can receive additional requests from the administrator client device(s) 1212 that include generating the virtual perturbed cells.

In some embodiments, the environment also includes additional device(s). For example, the latent transfer perturbation system 1202 can utilize the additional device(s) to further operate and manage the completion of complex drug discovery pipelines. For instance, the additional device(s) include experimental device(s) and analytical device(s). Further, in some instances, the additional device(s) also include the computing devices discussed below in connection with FIG. 14.

Furthermore, in one or more implementations, the administrator client device(s) 1212 include a client application 1214. The client application 1214 can include instructions that (upon execution) cause the administrator client device(s) 1212 to perform various actions. For example, a user of a user account can interact with the client application 1214 on the administrator client device(s) 1212 to execute experiments or other multi-faceted processes, to further access the latent transfer perturbation neural network 1203, and/or initiate a request to generate a virtual perturbed cell. For instance, in some embodiments the latent transfer perturbation system 1202 receives a request to generate a virtual perturbed cell, and in response generates the prediction and returns the virtual perturbed cell to the administrator client device(s) 1212. In some instances, the transmittal of the virtual perturbed cell to the administrator client device(s) 1212 causes the administrator client device(s) 1212 to execute an action (e.g., generate a downstream model prediction or other task).

The environment can also include experimental device(s) 1216. For example, the tech-bio exploration system 1204 can interact with experimental device(s) 1216 that include intelligent robotic devices and camera devices for generating and capturing digital images of cellular phenotypes resulting from different perturbations (e.g., genetic knockouts or compound treatments of stem cells). Similarly, the experimental device(s) 1216 can include camera devices and/or other sensors (e.g., heat or motion sensors) capturing real-time information from animals as part of in vivo experimentation. The tech-bio exploration system 1204 can also interact with a variety of other experimental device(s) 1216 such as devices for determining, generating, or extracting gene sequences or protein information. For example, the experimental device(s) 1216 may include computing devices linked to biosensors, electrophysiological platforms, x-ray crystallography machines, liquid chromatography mass spectrometry systems, nuclear magnetic resonance spectrometers, and/or mass spectrometers.

Additionally, the environment can include dedicated machine learning device(s) 1218. For example, the dedicated machine learning device(s) 1218 can include computing devices or virtual machines dedicated to training or implementing large-scale machine learning models. For example, the dedicated machine learning device(s) 1218 can generate machine learning predictions and/or embeddings based on digital biological data (e.g., digital images of phenotypes resulting from different perturbations or compound-protein interactions from compound features). Thus, the latent transfer perturbation system 1202 can interact with the dedicated machine learning device(s) to generate the phenomic similarity prediction.

As further shown in FIG. 12, the environment includes the network 1208. As mentioned above, the network 1208 can enable communication between components of the environment. In one or more embodiments, the network 1208 may include a suitable network and may communicate using a various number of communication platforms and technologies suitable for transmitting data and/or communication signals, examples of which are described with reference to FIG. 14. Furthermore, although FIG. 12 illustrates computing devices communicating via the network 1208, the various components of the environment can communicate and/or interact via other methods (e.g., communicate directly).

Figure 13:
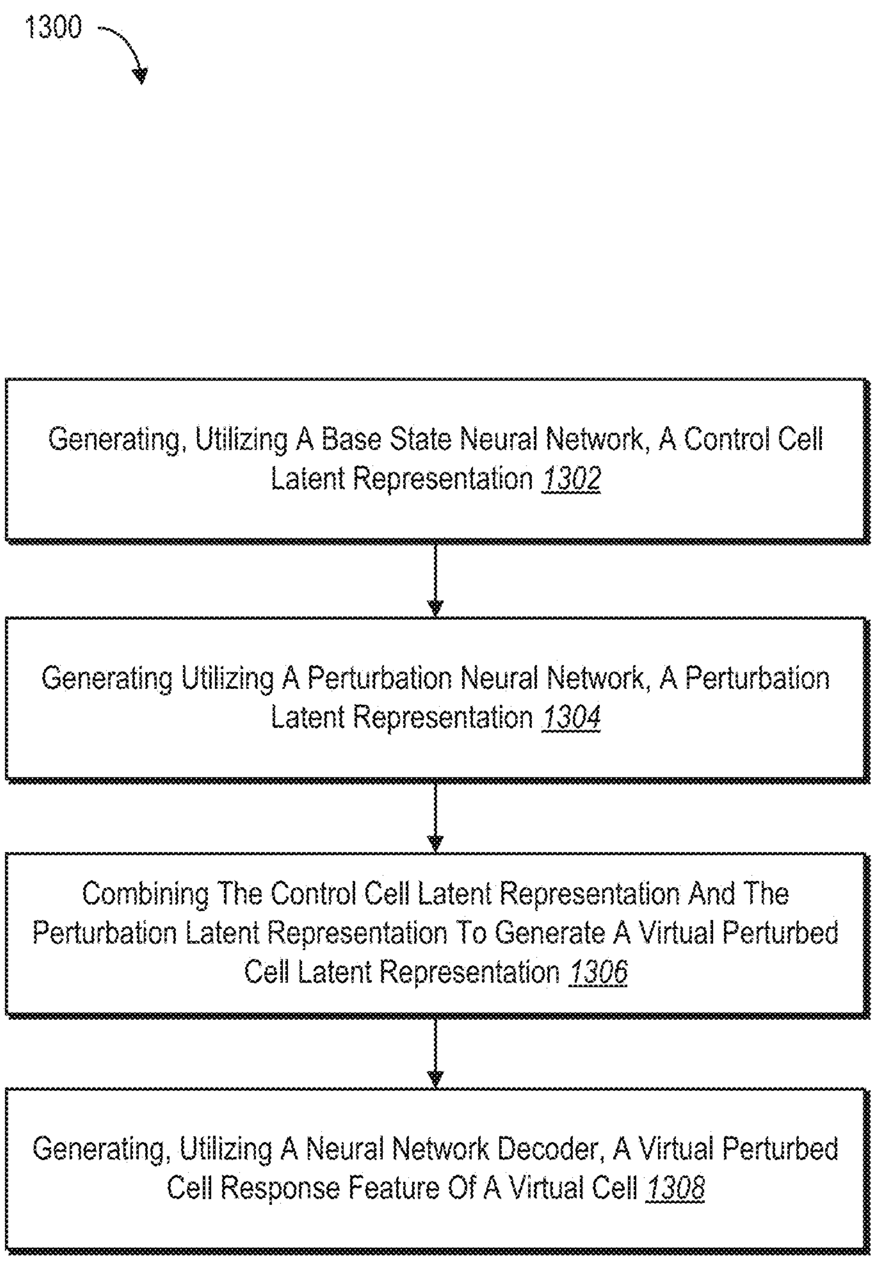
FIG. 13 illustrates a flowchart of a series of acts for generating a virtual perturbed cell in accordance with one or more embodiments.

FIGS. 1-12, the corresponding text, and the examples provide a number of different methods, systems, devices, and non-transitory computer-readable media of the latent transfer perturbation system. In addition to the foregoing, one or more embodiments can also be described in terms of flowcharts comprising acts for accomplishing a particular result, as shown in FIG. 13. FIG. 13 may be performed with more or fewer acts. Further, the acts may be performed in differing orders. Additionally, the acts described herein may be repeated or performed in parallel with one another or parallel with different instances of the same or similar acts.

As mentioned, FIG. 13 illustrates a flowchart of a series of acts 1300 for generating a virtual perturbed cell response feature of a virtual cell in accordance with one or more embodiments. While FIG. 13 illustrates acts according to one embodiment, alternative embodiments may omit, add to, reorder, and/or modify any of the acts shown in FIG. _. The acts of FIG. 13 can be performed as part of a method. Alternatively, a non-transitory computer-readable medium can comprise instructions that, when executed by one or more processors, cause a computing device to perform the acts of FIG. 13. In some embodiments, a system can perform the acts of FIG. 13.

As shown in FIG. 13, the series of acts 1300 can include an act 1302 for generating, utilizing a base state neural network, a control cell latent representation. To illustrate, the act 1302 can include generating, utilizing a base state neural network, a control cell latent representation from features extracted from a control cell.

Further, the series of acts 1300 can include an act 1304 of generating, utilizing a perturbation neural network, a perturbation latent representation. More specifically, the act 1302 can include generating utilizing a perturbation neural network, a perturbation latent representation for a perturbation from a multi-perturbation interaction data object.

Additionally, as shown in FIG. 13, the series of acts 1300 can include an act 1306 of combining the control cell latent representation and the perturbation latent representation to generate a virtual perturbed cell latent representation. To illustrate, the act 1306 can include combining the control cell latent representation and the perturbation latent representation to generate a virtual perturbed cell latent representation.

As also shown in FIG. 13, the series of acts 1300 can include an act 1308 of generating, utilizing a neural network decoder, a virtual perturbed cell response feature of a virtual cell. More specifically, the act 1306 can include generating, utilizing a neural network decoder, a virtual perturbed cell response feature of a virtual cell subject to the perturbation from the virtual perturbed cell latent representation.

Further, in one or more embodiments, the series of acts 1300 can include generating the multi-perturbation interaction data object by generating a perturbation interaction graph comprising perturbation nodes reflecting perturbations and perturbation interaction edges reflecting interactions between the perturbations, and generating, utilizing the perturbation neural network, the perturbation latent representation for the perturbation from the perturbation interaction graph. Additionally, in some embodiments, the series of acts 1300 includes wherein generating the control cell latent representation from features extracted from a control cell comprises identifying a gene expression profile for the control cell, and generating, utilizing an encoder of the neural network, the control cell latent representation from the gene expression profile for the control cell.

The series of acts 1300 can also include wherein generating the virtual perturbed cell response feature comprises generating a predicted gene expression profile of the virtual cell subject to the perturbation from the virtual perturbed cell latent representation. Additionally, the series of acts 1300 can also include extracting perturbation machine learning embeddings comprising at least one of phenomic image machine learning embeddings or transcriptomic profile machine learning embeddings from a functional response database, generating similarity metrics by comparing the perturbation machine learning embeddings, and generating the perturbation interaction edges utilizing the similarity metrics corresponding to the perturbation machine learning embeddings.

In one or more embodiments, the series of acts 1300 also includes generating the perturbation latent representation by generating a first multi-perturbation interaction graph from a first data repository, generating a second multi-perturbation interaction graph from a second data repository, and combining the first multi-perturbation interaction graph and the second multi-perturbation interaction graph to generate the perturbation latent representation. Further, in some embodiments, the series of acts 1300 includes generating, the perturbation latent representation from the perturbation interaction graph by utilizing a graph attention network to dynamically weight the perturbation interaction edges.

Further, in one or more embodiments, the series of acts 1300 also includes wherein combining the first multi-perturbation interaction graph and the second multi-perturbation interaction graph to generate the perturbation latent representation comprises, utilizing a first channel of a graph attention neural network to generate a first graph representation from the first multi-perturbation interaction graph, utilizing a second channel of the graph attention neural networks to generate a second graph representation from the second multi-perturbation interaction graph, and utilizing a combination model to generate the perturbation latent representation from the first graph representation and the second graph representation.

Additionally, in some embodiments, the series of acts 1300 includes wherein combining the first multi-perturbation interaction graph and the second multi-perturbation interaction graph to generate the perturbation latent representation comprises utilizing a graph transformer model to generate a union graph of combined perturbation nodes and the perturbation interaction edges from the first multi-perturbation interaction graph and the second multi-perturbation interaction graph, and generating the perturbation latent representation from the union graph.

Further, in one or more embodiments, the series of acts 1300 includes wherein combining the first multi-perturbation interaction graph and the second multi-perturbation interaction graph to generate the perturbation latent representation comprises generating a unified supra-adjacency representation of both the first multi-perturbation interaction graph and the second multi-perturbation interaction graph, wherein the unified supra-adjacency representation encodes intra-layer and inter-layer connections of the first multi-perturbation interaction graph and the second multi-perturbation interaction graph, and utilizing a graph attention transformer model for message passing across the intra-layer connections and the inter-layer connections of the unified supra-adjacency representation to generate the perturbation latent representation from the unified supra-adjacency representation.

Embodiments of the present disclosure may comprise or utilize a special purpose or general-purpose computer including computer hardware, such as, for example, one or more processors and system memory, as discussed in greater detail below. Embodiments within the scope of the present disclosure also include physical and other computer-readable media for carrying or storing computer-executable instructions and/or data structures. In particular, one or more of the processes described herein may be implemented at least in part as instructions embodied in a non-transitory computer-readable medium and executable by one or more computing devices (e.g., any of the media content access devices described herein). In general, a processor (e.g., a microprocessor) receives instructions, from a non-transitory computer-readable medium, (e.g., memory), and executes those instructions, thereby performing one or more processes, including one or more of the processes described herein.

Computer-readable media can be any available media that can be accessed by a general purpose or special purpose computer system. Computer-readable media that store computer-executable instructions are non-transitory computer-readable storage media (devices). Computer-readable media that carry computer-executable instructions are transmission media. Thus, by way of example, and not limitation, embodiments of the disclosure can comprise at least two distinctly different kinds of computer-readable media: non-transitory computer-readable storage media (devices) and transmission media.

Non-transitory computer-readable storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to non-transitory computer-readable storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that non-transitory computer-readable storage media (devices) can be included in computer system components that also (or even primarily) utilize transmission media.

Computer-executable instructions comprise, for example, instructions and data which, when executed by a processor, cause a general-purpose computer, special purpose computer, or special purpose processing device to perform a certain function or group of functions. In some embodiments, computer-executable instructions are executed by a general-purpose computer to turn the general-purpose computer into a special purpose computer implementing elements of the disclosure. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Embodiments of the present disclosure can also be implemented in cloud computing environments. As used herein, the term "cloud computing" refers to a model for enabling on-demand network access to a shared pool of configurable computing resources. For example, cloud computing can be employed in the marketplace to offer ubiquitous and convenient on-demand access to the shared pool of configurable computing resources. The shared pool of configurable computing resources can be rapidly provisioned via virtualization and released with low management effort or service provider interaction, and then scaled accordingly.

A cloud-computing model can be composed of various characteristics such as, for example, on-demand self-service, broad network access, resource pooling, rapid elasticity, measured service, and so forth. A cloud-computing model can also expose various service models, such as, for example, Software as a Service ("SaaS"), Platform as a Service ("PaaS"), and Infrastructure as a Service ("IaaS"). A cloud-computing model can also be deployed using different deployment models such as private cloud, community cloud, public cloud, hybrid cloud, and so forth. In addition, as used herein, the term "cloud-computing environment" refers to an environment in which cloud computing is employed.

Figure 14:
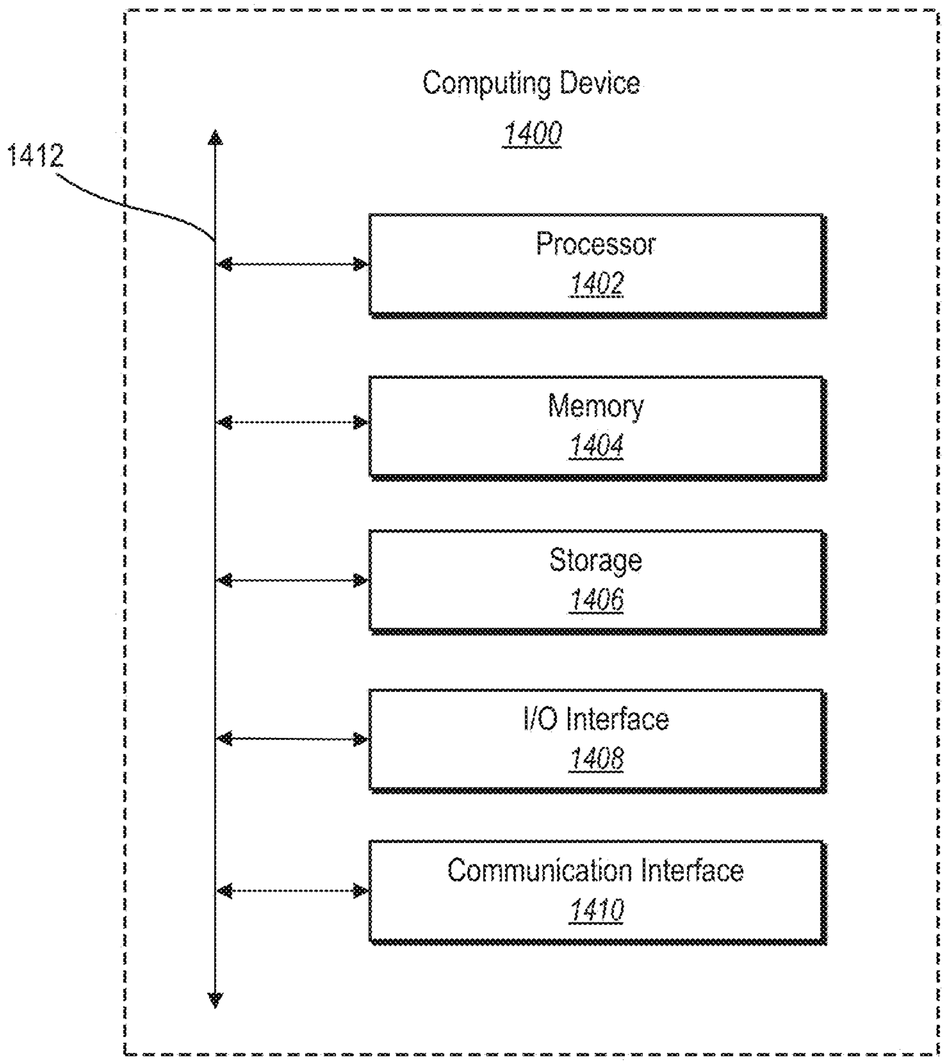
FIG. 14 illustrates a block diagram of an example computing device for implementing one or more embodiments of the present disclosure.

FIG. 14 illustrates a block diagram of an example computing device 1400 that may be configured to perform one or more of the processes described above. One will appreciate that one or more computing devices, such as the computing device 1400 may represent the computing devices described above (e.g., the server(s) 1206, the experimental device(s) 1216, the administrator client device(s) 1212). In one or more embodiments, the computing device 1400 may be a mobile device (e.g., a mobile telephone, a smartphone, a PDA, a tablet, a laptop, a camera, a tracker, a watch, a wearable device, etc.). In some embodiments, the computing device 1400 may be a non-mobile device (e.g., a desktop computer or another type of client device). Further, the computing device 1400 may be a server device that includes cloud-based processing and storage capabilities.

As shown in FIG. 14, the computing device 1400 can include one or more processor(s) 1402, memory 1404, a storage device 1406, input/output interfaces 1408 (or "I/O interfaces 1408"), and a communication interface 1410, which may be communicatively coupled by way of a communication infrastructure (e.g., bus 1412). While the computing device 1400 is shown in FIG. 14, the components illustrated in FIG. 14 are not intended to be limiting.

Additional or alternative components may be used in other embodiments. Furthermore, in certain embodiments, the computing device 1400 includes fewer components than those shown in FIG. 14. Components of the computing device 1400 shown in FIG. 14 will now be described in additional detail.

In particular embodiments, the processor(s) 1402 includes hardware for executing instructions, such as those making up a computer program. As an example, and not by way of limitation, to execute instructions, the processor(s) 1402 may retrieve (or fetch) the instructions from an internal register, an internal cache, memory 1404, or a storage device 1406 and decode and execute them.

The computing device 1400 includes memory 1404, which is coupled to the processor(s) 1402. The memory 1404 may be used for storing data, metadata, and programs for execution by the processor(s). The memory 1404 may include one or more of volatile and non-volatile memories, such as Random-Access Memory ("RAM"), Read-Only Memory ("ROM"), a solid-state disk ("SSD"), Flash, Phase Change Memory ("PCM"), or other types of data storage. The memory 1404 may be internal or distributed memory.

The computing device 1400 includes a storage device 1406 includes storage for storing data or instructions. As an example, and not by way of limitation, the storage device 1406 can include a non-transitory storage medium described above. The storage device 1406 may include a hard disk drive (HDD), flash memory, a Universal Serial Bus (USB) drive or a combination these or other storage devices.

As shown, the computing device 1400 includes one or more I/O interfaces 1408, which are provided to allow a user to provide input to (such as user strokes), receive output from, and otherwise transfer data to and from the computing device 1400. These I/O interfaces 1408 may include a mouse, keypad or a keyboard, a touch screen, camera, optical scanner, network interface, modem, other known I/O devices or a combination of such I/O interfaces 1408. The touch screen may be activated with a stylus or a finger.

The I/O interfaces 1408 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O interfaces 1408 are configured to provide graphical data to a display for presentation to a user. The graphical data may be representative of one or more graphical user interfaces and/or any other graphical content as may serve a particular implementation.

The computing device 1400 can further include a communication interface 1410. The communication interface 1410 can include hardware, software, or both. The communication interface 1410 provides one or more interfaces for communication (such as, for example, packet-based communication) between the computing device and one or more other computing devices or one or more networks. As an example, and not by way of limitation, communication interface 1410 may include a network interface controller (NIC) or network adapter for communicating with an Ethernet or other wire-based network or a wireless NIC (WNIC) or wireless adapter for communicating with a wireless network, such as a WI-FI. The computing device 1400 can further include a bus 1412. The bus 1412 can include hardware, software, or both that connects components of computing device 1400 to each other.

In the foregoing specification, the invention has been described with reference to specific example embodiments thereof. Various embodiments and aspects of the invention(s) are described with reference to details discussed herein, and the accompanying drawings illustrate the various embodiments. The description above and drawings are illustrative of the invention and are not to be construed as limiting the invention. Numerous specific details are described to provide a thorough understanding of various embodiments of the present invention.

The present invention may be embodied in other specific forms without departing from its spirit or essential characteristics. The described embodiments are to be considered in all respects only as illustrative and not restrictive. For example, the methods described herein may be performed with less or more steps/acts or the steps/acts may be performed in differing orders. Additionally, the steps/acts described herein may be repeated or performed in parallel to one another or in parallel to different instances of the same or similar steps/acts. The scope of the invention is, therefore, indicated by the appended claims rather than by the foregoing description. All changes that come within the meaning and range of equivalency of the claims are to be embraced within their scope.

What is claimed is:

1. A computer-implemented method comprising:

generating, based on functional response data corresponding to phenomic or transcriptomic responses to cellular perturbations, cellular perturbation machine learning embeddings within a latent machine learning feature space comprising at least one of phenomic image machine learning embeddings or transcriptomic profile machine learning embeddings;

determining pairwise similarity metrics among the cellular perturbation machine learning embeddings based on alignment of the cellular perturbation machine learning embeddings within the latent machine learning feature space;

generating a multi-perturbation interaction data object corresponding to relationships among the functional response data by constructing a unified representation of phenomic or transcriptomic interactions among the cellular perturbation machine learning embeddings utilizing the pairwise similarity metrics among the cellular perturbation machine learning embeddings;

generating, utilizing a base state neural network, a control cell latent representation from features extracted from a control cell;

generating, utilizing a perturbation neural network, a perturbation latent representation for a perturbation from the multi-perturbation interaction data object;

generating a virtual perturbed cell latent representation by combining the control cell latent representation and the perturbation latent representation such that the virtual perturbed cell latent representation reflects phenomic or transcriptomic attributes of the perturbation from the multi-perturbation interaction data object applied to the control cell; and generating, utilizing a neural network decoder, a virtual perturbed cell response feature of a virtual cell subject to the perturbation from the virtual perturbed cell latent representation.

2. The computer-implemented method of claim 1, further comprising:

generating the multi-perturbation interaction data object by generating a perturbation interaction graph comprising perturbation nodes reflecting perturbations and perturbation interaction edges reflecting interactions between the perturbations; and generating, utilizing the perturbation neural network, the perturbation latent representation for the perturbation from the perturbation interaction graph.

3. The computer-implemented method of claim 2, wherein generating the control cell latent representation from the features extracted from the control cell comprises:

identifying a gene expression profile for the control cell; and generating, utilizing an encoder of the base state neural network, the control cell latent representation from the gene expression profile for the control cell.

4. The computer-implemented method of claim 3, wherein generating the virtual perturbed cell response feature comprises generating a predicted gene expression profile of the virtual cell subject to the perturbation from the virtual perturbed cell latent representation.

5. The computer-implemented method of claim 2, further comprising:

extracting the cellular perturbation machine learning embeddings comprising at least one of the phenomic image machine learning embeddings or the transcriptomic profile machine learning embeddings from a functional response database; and generating the perturbation interaction edges utilizing the pairwise similarity metrics corresponding to the cellular perturbation machine learning embeddings.

6. The computer-implemented method of claim 2, further comprising generating the perturbation latent representation by:

generating a first multi-perturbation interaction graph from a first data repository;

generating a second multi-perturbation interaction graph from a second data repository; and combining the first multi-perturbation interaction graph and the second multi-perturbation interaction graph to generate the perturbation latent representation.

7. The computer-implemented method of claim 6, wherein combining the first multi-perturbation interaction graph and the second multi-perturbation interaction graph to generate the perturbation latent representation comprises:

utilizing a first channel of a graph attention neural network to generate a first graph representation from the first multi-perturbation interaction graph;

utilizing a second channel of the graph attention neural network to generate a second graph representation from the second multi-perturbation interaction graph; and utilizing a combination model to generate the perturbation latent representation from the first graph representation and the second graph representation.

8. The computer-implemented method of claim 6, wherein combining the first multi-perturbation interaction graph and the second multi-perturbation interaction graph to generate the perturbation latent representation comprises:

utilizing a graph transformer model to generate a union graph of combined perturbation nodes and the perturbation interaction edges from the first multi-perturbation interaction graph and the second multi-perturbation interaction graph; and generating the perturbation latent representation from the union graph.

9. The computer-implemented method of claim 6, wherein combining the first multi-perturbation interaction graph and the second multi-perturbation interaction graph to generate the perturbation latent representation comprises:

generating a unified supra-adjacency representation of both the first multi-perturbation interaction graph and the second multi-perturbation interaction graph, wherein the unified supra-adjacency representation encodes intra-layer and inter-layer connections of the first multi-perturbation interaction graph and the second multi-perturbation interaction graph; and utilizing a graph attention transformer model for message passing across the intra-layer and inter-layer connections of the unified supra-adjacency representation to generate the perturbation latent representation from the unified supra-adjacency representation.

10. The computer-implemented method of claim 2, further comprising generating, the perturbation latent representation from the perturbation interaction graph by utilizing a graph attention network to dynamically weight the perturbation interaction edges.

11. A system comprising:

at least one processor; and at least one non-transitory computer-readable storage medium storing instructions that, when executed by the at least one processor, cause the system to:

generate, based on functional response data corresponding to phenomic or transcriptomic responses to cellular perturbations, cellular perturbation machine learning embeddings within a latent machine learning feature space comprising at least one of phenomic image machine learning embeddings or transcriptomic profile machine learning embeddings;

determine pairwise similarity metrics among the cellular perturbation machine learning embeddings on alignment of the cellular perturbation machine learning embeddings within the latent machine learning feature space;

generate a multi-perturbation interaction data object corresponding to relationships among the functional response data by constructing a unified representation of phenomic or transcriptomic interactions among the cellular perturbation machine learning embeddings utilizing the pairwise similarity metrics among the cellular perturbation machine learning embeddings;

generate, utilizing a base state neural network, a control cell latent representation from features extracted from a control cell;

generate, utilizing a perturbation neural network, a perturbation latent representation for a perturbation from the multi-perturbation interaction data object;

generate a virtual perturbed cell latent representation by combining the control cell latent representation and the perturbation latent representation such that the virtual perturbed cell latent representation reflects phenomic or transcriptomic attributes of the perturbation from the multi-perturbation interaction data object applied to the control cell; and generate, utilizing a neural network decoder, a virtual perturbed cell response feature of a virtual cell subject to the perturbation from the virtual perturbed cell latent representation.

12. The system of claim 11, wherein the at least one non-transitory computer-readable storage medium stores additional instructions that, when executed by the at least one processor, cause the system to:

generate the multi-perturbation interaction data object by generating a perturbation interaction graph comprising perturbation nodes reflecting perturbations and perturbation interaction edges reflecting interactions between the perturbations; and generate, utilizing the perturbation neural network, the perturbation latent representation for the perturbation from the perturbation interaction graph.

13. The system of claim 12, wherein the at least one non-transitory computer-readable storage medium stores additional instructions that, when executed by the at least one processor, cause the system to generate the control cell latent representation from the features extracted from the control cell by:

identifying a gene expression profile for the control cell; and generating, utilizing an encoder of the base state neural network, the control cell latent representation from the gene expression profile for the control cell.

14. The system of claim 13, wherein the at least one non-transitory computer-readable storage medium stores additional instructions that, when executed by the at least one processor, cause the system to generate the virtual perturbed cell response feature by generating a predicted gene expression profile of the virtual cell subject to the perturbation from the virtual perturbed cell latent representation.

15. The system of claim 12, wherein the at least one non-transitory computer-readable storage medium stores additional instructions that, when executed by the at least one processor, cause the system to:

extract the cellular perturbation machine learning embeddings comprising at least one of the phenomic image machine learning embeddings or the transcriptomic profile machine learning embeddings from a functional response database; and generate the perturbation interaction edges utilizing the pairwise similarity metrics corresponding to the cellular perturbation machine learning embeddings.

16. A non-transitory computer-readable medium storing instructions that, when executed by at least one processor, cause a computing device to:

generate, based on functional response data corresponding to phenomic or transcriptomic responses to cellular perturbations, cellular perturbation machine learning embeddings within a latent machine learning feature space comprising at least one of phenomic image machine learning embeddings or transcriptomic profile machine learning embeddings;

determine pairwise similarity metrics among the cellular perturbation machine learning embeddings on alignment of the cellular perturbation machine learning embeddings within the latent machine learning feature space;

generate a multi-perturbation interaction data object corresponding to relationships among the functional response data by constructing a unified representation of phenomic or transcriptomic interactions among the cellular perturbation machine learning embeddings utilizing the pairwise similarity metrics among the cellular perturbation machine learning embeddings;

generate, utilizing a base state neural network, a control cell latent representation from features extracted from a control cell;

generate, utilizing a perturbation neural network, a perturbation latent representation for a perturbation from the multi-perturbation interaction data object;

generate a virtual perturbed cell latent representation by combining the control cell latent representation and the perturbation latent representation such that the virtual perturbed cell latent representation reflects phenomic or transcriptomic attributes of the perturbation from the multi-perturbation interaction data object applied to the control cell; and generate, utilizing a neural network decoder, a virtual perturbed cell response feature of a virtual cell subject to the perturbation from the virtual perturbed cell latent representation.

17. The non-transitory computer-readable medium of claim 16, further storing additional instructions that, when executed by the at least one processor, cause the computing device to:

generate the multi-perturbation interaction data object by generating a perturbation interaction graph comprising perturbation nodes reflecting perturbations and perturbation interaction edges reflecting interactions between the perturbations; and generate, utilizing the perturbation neural network, the perturbation latent representation for the perturbation from the perturbation interaction graph.

18. The non-transitory computer-readable medium of claim 17, further storing additional instructions that, when executed by the at least one processor, cause the computing device to generate the control cell latent representation from the features extracted from the control cell by:

identifying a gene expression profile for the control cell; and generating, utilizing an encoder of the base state neural network, the control cell latent representation from the gene expression profile for the control cell.

19. The non-transitory computer-readable medium of claim 18, further storing additional instructions that, when executed by the at least one processor, cause the computing device to generate the virtual perturbed cell response feature by generating a predicted gene expression profile of the virtual cell subject to the perturbation from the virtual perturbed cell latent representation.

20. The non-transitory computer-readable medium of claim 17, further storing additional instructions that, when executed by the at least one processor, cause the computing device to:

extract the cellular perturbation machine learning embeddings comprising at least one of the phenomic image machine learning embeddings or the transcriptomic profile machine learning embeddings from a functional response database; and generate the perturbation interaction edges utilizing the pairwise similarity metrics corresponding to the cellular perturbation machine learning embeddings.

* * * * *